United States Patent
Endo et al.

(10) Patent No.: US 9,469,777 B2
(45) Date of Patent: Oct. 18, 2016

(54) RESIST UNDERLAYER FILM FORMING COMPOSITION THAT CONTAINS NOVOLAC RESIN HAVING POLYNUCLEAR PHENOL

(71) Applicant: NISSAN CHEMICAL INDUSTRIES, LTD., Tokyo (JP)

(72) Inventors: Takafumi Endo, Toyama (JP); Tetsuya Shinjo, Toyama (JP); Keisuke Hashimoto, Toyama (JP); Yasunobu Someya, Toyama (JP); Hirokazu Nishimaki, Toyama (JP); Ryo Karasawa, Toyama (JP); Rikimaru Sakamoto, Toyama (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/415,040

(22) PCT Filed: Aug. 13, 2013

(86) PCT No.: PCT/JP2013/071870
§ 371 (c)(1),
(2) Date: Jan. 15, 2015

(87) PCT Pub. No.: WO2014/030579
PCT Pub. Date: Feb. 27, 2014

(65) Prior Publication Data
US 2015/0184018 A1    Jul. 2, 2015

(30) Foreign Application Priority Data

Aug. 21, 2012  (JP) ................. 2012-182562

(51) Int. Cl.
*G03F 7/004*    (2006.01)
*C09D 161/12*   (2006.01)
*C07C 39/15*    (2006.01)
*G03F 7/038*    (2006.01)
*G03F 7/11*     (2006.01)
*H01L 21/027*   (2006.01)
*C08G 8/02*     (2006.01)
*C08G 8/04*     (2006.01)
*C09D 161/04*   (2006.01)
*H01L 21/308*   (2006.01)
*H01L 21/311*   (2006.01)

(52) U.S. Cl.
CPC ............ *C09D 161/12* (2013.01); *C07C 39/15* (2013.01); *C08G 8/02* (2013.01); *C08G 8/04* (2013.01); *C09D 161/04* (2013.01); *G03F 7/038* (2013.01); *G03F 7/11* (2013.01); *H01L 21/0271* (2013.01); *H01L 21/3088* (2013.01); *H01L 21/31144* (2013.01); *H01L 21/31138* (2013.01)

(58) Field of Classification Search
CPC ... C09D 161/04; C09D 161/12; G03F 7/038; G03F 7/0382; G03F 7/039; G03F 7/40; C08G 8/02; C08G 8/04; H01L 21/0271; H01L 21/3088; H01L 21/31138; H01L 21/31144; C07C 39/04; C07C 39/15; C07C 2103/74
USPC .......... 430/270.1, 271.1, 311, 313, 314, 317, 430/322, 325, 329, 330, 331; 524/594; 438/703; 568/720, 717, 426, 439, 722
See application file for complete search history.

(56) References Cited

U.S. PATENT DOCUMENTS

| | | | |
|---|---|---|---|
| 4,474,929 A * | 10/1984 | Schrader | C07D 303/24 525/480 |
| 7,378,217 B2 | 5/2008 | Oh et al. | |
| 8,652,757 B2 * | 2/2014 | Hatakeyama | G03F 7/095 430/270.1 |
| 9,170,495 B2 * | 10/2015 | Kim | C07D 491/107 |
| 2009/0182175 A1 * | 7/2009 | Yoshitomo | C07C 45/565 568/442 |
| 2010/0099044 A1 * | 4/2010 | Hatakeyama | G03F 7/095 430/285.1 |
| 2010/0099908 A1 * | 4/2010 | Yoshitomo | C07C 39/15 560/53 |
| 2011/0172457 A1 * | 7/2011 | Yoshitomo | C07C 39/17 560/53 |

| | | | |
|---|---|---|---|
| 2011/0177459 A1 | 7/2011 | Ogihara et al. | |
| 2012/0108071 A1 | 5/2012 | Ogihara et al. | |
| 2012/0277479 A1* | 11/2012 | Iwai | C07C 39/17 568/720 |
| 2013/0280913 A1* | 10/2013 | Shinjo | C09D 139/04 438/694 |
| 2013/0341304 A1* | 12/2013 | Minegishi | C08F 220/18 216/47 |
| 2014/0319659 A1* | 10/2014 | Kwon | G03F 7/092 257/632 |
| 2015/0212418 A1* | 7/2015 | Nishimaki | C08G 8/04 438/703 |
| 2015/0267046 A1* | 9/2015 | Namai | C08L 47/00 216/49 |

FOREIGN PATENT DOCUMENTS

| | | |
|---|---|---|
| JP | H01-154050 A | 6/1989 |
| JP | H02-022657 A | 1/1990 |
| JP | H02-293850 A | 12/1990 |
| JP | 2005-128509 A | 5/2005 |
| JP | 2006-259249 A | 9/2006 |
| JP | 2006-259482 A | 9/2006 |
| JP | 2007-178974 A | 7/2007 |
| JP | 2007-199653 A | 8/2007 |
| JP | 2010-117629 A | 5/2010 |
| JP | 2010-170013 A | 8/2010 |
| JP | 2011-150023 A | 8/2011 |
| JP | 2012-098431 A | 5/2012 |
| WO | 2007/097457 A1 | 8/2007 |
| WO | 2010/147155 A1 | 12/2010 |

OTHER PUBLICATIONS

Machine translation of Jp 2007-199653 (no. date).*
Oct. 15, 2013 International Search Report issued in International Application No. PCT/JP2013/071870.

\* cited by examiner

*Primary Examiner* — Amanda C Walke
(74) *Attorney, Agent, or Firm* — Oliff PLC

(57) ABSTRACT

There is provided a composition for forming a resist underlayer film which has high dry-etching resistance and wiggling resistance, and achieves excellent planarizing properties for a semiconductor substrate surface having level differences or irregular portions. A resist underlayer film-forming composition including a phenol novolac resin that is obtained by causing a compound that has at least three phenolic groups, in which each of the phenolic groups has a structure bonded to a tertiary carbon atom or has a structure bonded to a quaternary carbon atom to which a methyl group binds, to react with an aromatic aldehyde or an aromatic ketone in the presence of an acid catalyst. The phenol novolac resin preferably contains a unit structure of Formula (1), a unit structure of Formula (2), a unit structure of Formula (3), a unit structure of Formula (4), or a combination of these unit structures:

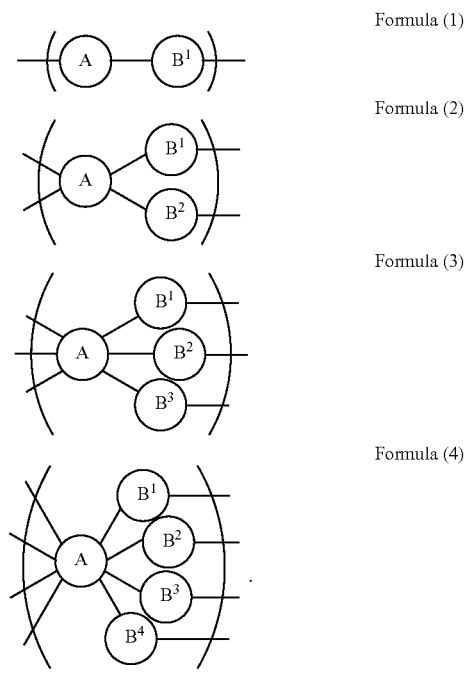

12 Claims, 6 Drawing Sheets

RESIST UNDERLAYER FILM FORMING COMPOSITION THAT CONTAINS NOVOLAC RESIN HAVING POLYNUCLEAR PHENOL

TECHNICAL FIELD

The present invention relates to a resist underlayer film-forming composition for lithography that is useful in fabricating a semiconductor substrate, a resist pattern forming method using the resist underlayer film-forming composition, and a method for producing a semiconductor device.

BACKGROUND ART

Conventionally, microfabrication by lithography using photoresist compositions has been performed in the production of semiconductor devices. This microfabrication is a fabrication method that includes forming a thin film of a photoresist composition on a substrate to be fabricated such as a silicon wafer, irradiating active rays such as ultraviolet rays onto the thin film through a mask pattern in which a pattern of a semiconductor device is formed, developing the film, and etching the substrate to be fabricated such as a silicon wafer using the obtained photoresist pattern as a protective film. In recent years, higher integration of semiconductor devices has been pursued, and there is a trend for the active rays used to have shorter wavelengths from KrF excimer lasers (248 nm) to ArF excimer lasers (193 nm). This trend has been accompanied by significant issues of influences due to standing waves and diffuse reflection of the active rays by irradiation from the substrate. Accordingly, methods have been extensively studied that include providing an anti-reflective coating (Bottom Anti-Reflective Coating, BARC) between the photoresist and the substrate to be fabricated.

As a finer resist pattern is further pursued, an issue of resolution and an issue in which the resist pattern formed collapses after development may occur, and thus thinner resists are required to solve these issues. However, in producing such thinner resists, it is difficult to achieve sufficient resist pattern film thickness for fabrication of a substrate, and thus a process has become necessary in which the function of a mask during the substrate fabrication is imparted not only to the resist pattern, but also to a resist underlayer film that is formed between the resist and a semiconductor substrate to be fabricated. As a method for achieving such a thinner film thickness of resists, a lithography process is known in which at least two layers of resist underlayer films are formed, and the resist underlayer films are used as etching masks. The resist underlayer films for the lithography process need to have high etching resistance to an etching gas (e.g., fluorocarbon) in a dry etching process.

As the resist pattern becomes finer, irregular bending of the pattern called "wiggling" may occur in the resist underlayer films as etching masks during a dry-etching process, thereby hindering desired pattern formation during the semiconductor substrate fabrication. Thus, the resist underlayer films as etching masks require underlayer film material having high wiggling resistance that can suppress occurrence of the wiggling even in fine patterns. The resist underlayer films also require a resist underlayer film-forming composition having planarizing properties and embeddability that enable level differences or irregular portions formed on surfaces of semiconductor substrates to be sufficiently coated.

The following are examples of a polymer for the resist underlayer film described above.

Resist underlayer film-forming compositions each including polyvinyl carbazole are exemplified (see Patent Document 1, Patent Document 2, and Patent Document 3).

A resist underlayer film-forming composition including a fluorene phenol novolac resin is described (see Patent Document 4, for example).

A resist underlayer film-forming composition including a fluorene naphthol novolac resin is described (see Patent Document 5, for example).

Resist underlayer film-forming compositions each containing fluorene phenol and aryl alkylene as repeating units are described (see Patent Document 6 and Patent Document 7, for example).

A resist underlayer film-forming composition including carbazole novolac is described (see Patent Document 8, for example).

A resist underlayer film-forming composition including a polynuclear phenol novolac is described (see Patent Document 9, for example).

PRIOR ART DOCUMENTS

Patent Documents

Patent Document 1: Japanese Patent Application Publication No. 2-293850.
Patent Document 2: Japanese Patent Application Publication No. 1-154050
Patent Document 3: Japanese Patent Application Publication No. 2-22657
Patent Document 4: Japanese Patent Application Publication No. 2005-128509
Patent Document 5: Japanese Patent Application Publication No. 2007-199653
Patent Document 6: Japanese Patent Application Publication No. 2007-178974
Patent Document 7: U.S. Pat. No. 7,378,217
Patent Document 8: International Publication No. WO2010-147155 pamphlet
Patent Document 9: Japanese Patent Application Publication No. 2006-259249

SUMMARY OF THE INVENTION

Problem to be Solved by the Invention

An object of the present invention is to provide a resist underlayer film-forming composition used in a lithography process of semiconductor device production. Another object of the present invention is to provide a resist underlayer film-forming composition having high dry-etching resistance to an etching gas such as fluorocarbon, and can suppress occurrence of the wiggling in a resist underlayer film during a dry-etching process to achieve finer semiconductor substrate fabrication. Still another object of the present invention is to provide a coating-type resist underlayer film-forming composition having high solubility in a resist solvent and being spin-coatable to achieve excellent planarizing properties and embeddability for a semiconductor substrate surface having level differences or irregular portions.

Means for Solving the Problem

The invention of the present application provides, as a first aspect, a resist underlayer film-forming composition comprising: a phenol novolac resin that is obtained by causing a compound that has at least three phenolic groups, in which each of the phenolic groups has a structure bonded to a tertiary carbon atom or has a structure bonded to a quaternary carbon atom to which a methyl group binds, to react with an aromatic aldehyde or an aromatic ketone in the presence of an acid catalyst;

as a second aspect, the resist underlayer film-forming composition according to the first aspect, in which the phenol novolac resin contains a unit structure of Formula (1), a unit structure of Formula (2), a unit structure of Formula (3), a unit structure of Formula (4), or a combination of these unit structures:

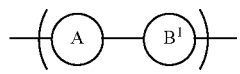

Formula (1)

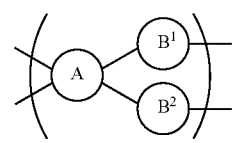

Formula (2)

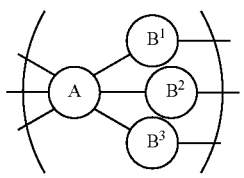

Formula (3)

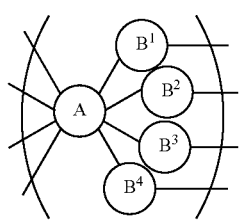

Formula (4)

(in Formulae (1) to (4), A is an organic group having at least three phenolic groups, in which each of the phenolic groups has a structure bonded to a tertiary carbon atom, and each of $B^1$, $B^2$, $B^3$, and $B^4$ is Formula (5):

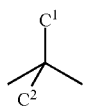

Formula (5)

(in Formula (5), $C^1$ is a $C_{6-40}$ aryl group or a heterocyclic group that is optionally substituted with a halogen group, a nitro group, an amino group, or a hydroxy group; $C^2$ is a hydrogen atom or a $C_{1-10}$ alkyl group, a $C_{6-40}$ aryl group, or a heterocyclic group each of which is optionally substituted with a halogen group, a nitro group, an amino group, or a hydroxy group; and $C^1$ and $C^2$ optionally form a ring together with a carbon atom bonded to $C^1$ and $C^2$));

as a third aspect, the resist underlayer film-forming composition according to the second aspect, in which A is Formula (6):

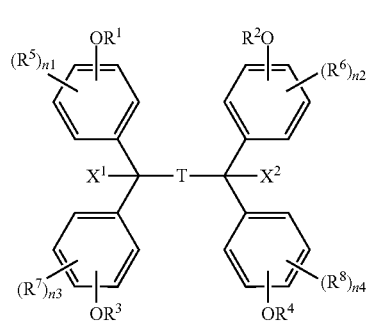

Formula (6)

(in Formula (6), T is a single bond, a $C_{1-10}$ alkylene group, or a $C_{6-40}$ arylene group; $X^1$ and $X^2$ each are a hydrogen atom or a methyl group; $R^1$ to $R^4$ each are a hydrogen atom or a $C_{1-10}$ alkyl group; $R^5$ to $R^8$ each are a $C_{1-10}$ alkyl group or a $C_{6-40}$ aryl group; n1 to n4 each are an integer of 0 to 3; and each of the phenolic groups appropriately binds to $B^1$, $B^2$, $B^3$, and $B^4$);

as a fourth aspect, the resist underlayer film-forming composition according to the second aspect, in which A is Formula (7):

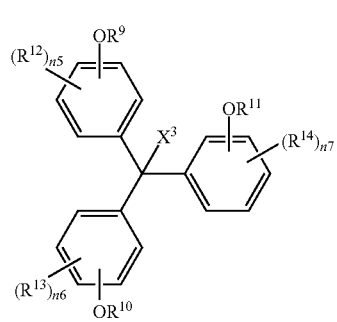

Formula (7)

(in Formula (7), $R^9$ to $R^{11}$ each are a hydrogen atom or a $C_{1-10}$ alkyl group; $R^{12}$ to $R^{14}$ each are a $C_{1-10}$ alkyl group or a $C_{6-40}$ aryl group; $X^3$ is a hydrogen atom or a methyl group; n5 to n7 each are an integer of 0 to 3; and each of the phenolic groups appropriately binds to $B^1$, $B^2$, $B^3$, and $B^4$);

as a fifth aspect, the resist underlayer film-forming composition according to any one of the second aspect to the fourth aspect, in which $C^1$ is an anthryl group or a pyrenyl group;

as a sixth aspect, the resist underlayer film-forming composition according to any one of the first aspect to the fourth aspect, further comprising: a cross-linking agent;

as a seventh aspect, the resist underlayer film-forming composition according to any one of the first aspect to the fifth aspect, further comprising: an acid and/or an acid generator;

as an eighth aspect, a resist underlayer film obtained by applying the resist underlayer film-forming composition as described in any one of the first aspect to the seventh aspect onto a semiconductor substrate and baking the resist underlayer film-forming composition;

as a ninth aspect, a method for forming a resist pattern used in production of a semiconductor, the method comprising: applying the resist underlayer film-forming composition as described in any one of the first aspect to the seventh aspect onto a semiconductor substrate and baking the resist underlayer film-forming composition to form an underlayer film;

as a tenth aspect, a method for producing a semiconductor device, the method comprising: forming an underlayer film on a semiconductor substrate using the resist underlayer film-forming composition as described in any one of the first aspect to the seventh aspect; forming a resist film on the underlayer film; forming a resist pattern by irradiation with light or an electron beam and development; etching the underlayer film using the resist pattern; and fabricating the semiconductor substrate using the underlayer film patterned;

as an eleventh aspect, a method for producing a semiconductor device, the method comprising: forming an underlayer film on a semiconductor substrate using the resist underlayer film-forming composition as described in any one of the first aspect to the seventh aspect; forming a hard mask on the underlayer film; further forming a resist film on the hard mask; forming a resist pattern by irradiation with light or an electron beam and development; etching the hard mask using the resist pattern; etching the underlayer film using the hard mask patterned; and fabricating the semiconductor substrate using the underlayer film patterned; and as a twelfth aspect, the method for producing the semiconductor device according to the eleventh aspect, in which the hard mask is formed by evaporation of an inorganic substance.

Effects of the Invention

With the resist underlayer film-forming composition of the present invention, an excellent resist underlayer film can be provided that has high dry-etching resistance to an etching gas such as fluorocarbon.

As a resist pattern becomes finer, a resist is made thinner in order to prevent the resist pattern from collapsing after development. For such a thin film resist, there are a process that includes transferring a resist pattern onto a underlayer film thereof in an etching process to fabricate a substrate using the underlayer film as a mask, and also a process that includes repeating steps of transferring a resist pattern onto a underlayer film in an etching process and further transferring the pattern transferred on the underlayer film onto an underlayer film thereof using a different etching gas to finally fabricate a substrate. The resist underlayer film and the composition for forming the resist underlayer film of the present invention are effective in such processes and, when a substrate is fabricated with the resist underlayer film of the present invention, exhibit sufficient etching resistance for the fabricated substrate (e.g., a thermal silicon oxide film, a silicon nitride film, or a polysilicon film on the substrate).

The resist underlayer film of the present invention can be used as a planarizing film, a resist underlayer film, an antifouling film for a resist layer, or a film having dry etching selectivity. This makes it possible to form a resist pattern easily and precisely in a lithography process of semiconductor production. In particular, occurrence of wiggling (irregular bending of patterns) of the resist underlayer film can be suppressed in a dry-etching process. Furthermore, the resist underlayer film-forming composition of the present invention has excellent planarizing properties and embeddability that enable a semiconductor substrate surface having level differences or irregular portions to be coated without irregularities or voids.

There is a process that includes forming a resist underlayer film on a substrate using the resist underlayer film-forming composition of the present invention; forming a hard mask thereon; forming a resist film thereon; forming a resist pattern by exposure and development; transferring the resist pattern onto the hard mask; transferring the resist pattern transferred on the hard mask to the resist underlayer film; and fabricating the semiconductor substrate using the resultant resist underlayer film. In this process, the hard mask may be formed out of a coating-type composition that contains an organic polymer or an inorganic polymer and a solvent, or may be formed by vacuum evaporation of an inorganic substance. The inorganic substance (e.g., silicon oxynitride) forms a deposit on the surface of the resist underlayer film upon vacuum evaporation, during which the temperature of the resist underlayer film surface rises to about 400° C. Because the polymer used in the present invention is a novolac resin of Formula (1), Formula (2), Formula (3), Formula (4), or a combination thereof, the resist underlayer film of the present invention has very high heat resistance, and does not undergo thermal degradation even through deposition of deposits. Furthermore, the resist underlayer film-forming composition of the present invention is a coating-type composition having high solubility in a resist solvent and excellent spin-coatability.

MODES FOR CARRYING OUT THE INVENTION

Figure 1:
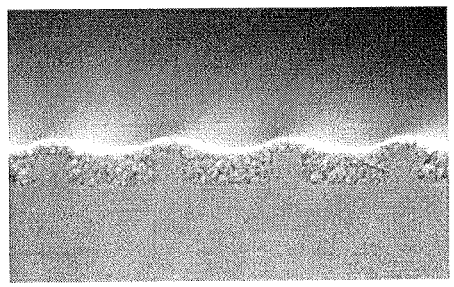
FIG. 1 is a cross-sectional SEM photograph indicating a planarizing property test result of Example 1 (at a magnification of 100,000).
Figure 2:
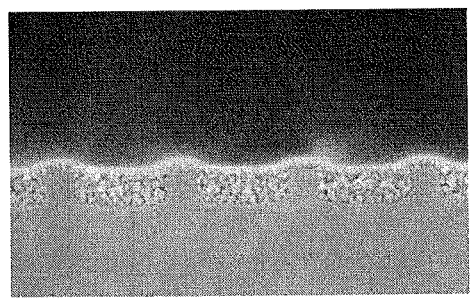
FIG. 2 is a cross-sectional SEM photograph indicating a planarizing property test result of Example 3 (at a magnification of 100,000).
Figure 3:
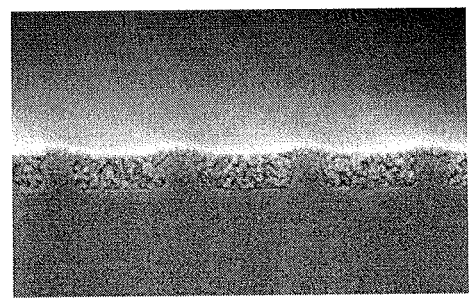
FIG. 3 is a cross-sectional SEM photograph indicating a planarizing property test result of Example 4 (at a magnification of 100,000).
Figure 4:
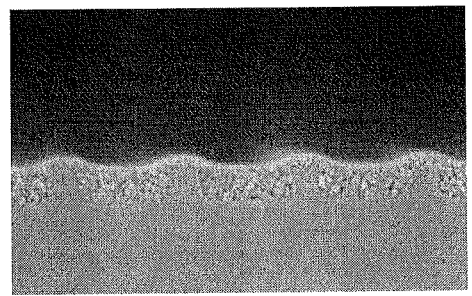
FIG. 4 is a cross-sectional SEM photograph indicating a planarizing property test result of Example 6 (at a magnification of 100,000).
Figure 5:
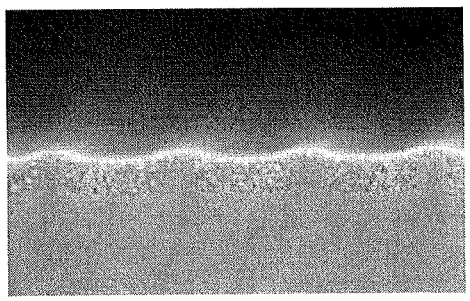
FIG. 5 is a cross-sectional SEM photograph indicating a planarizing property test result of Example 7 (at a magnification of 100,000).
Figure 6:
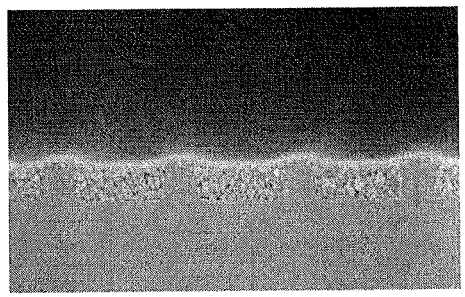
FIG. 6 is a cross-sectional SEM photograph indicating a planarizing property test result of Example 8 (at a magnification of 100,000).
Figure 7:
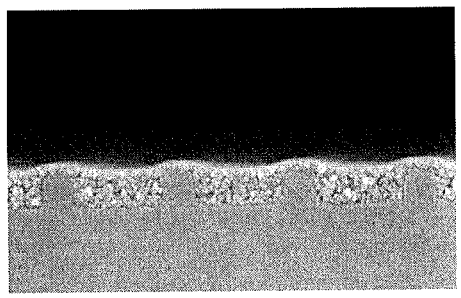
FIG. 7 is a cross-sectional SEM photograph indicating a planarizing property test result of Example 9 (at a magnification of 100,000).
Figure 8:
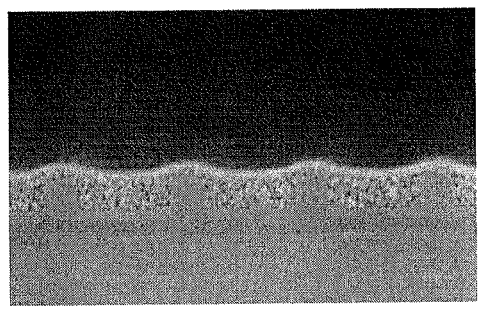
FIG. 8 is a cross-sectional SEM photograph indicating a planarizing property test result of Example 10 (at a magnification of 100,000).
Figure 9:
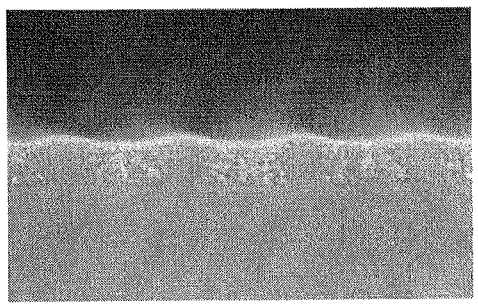
FIG. 9 is a cross-sectional SEM photograph indicating a planarizing property test result of Example 11 (at a magnification of 100,000).
Figure 10:
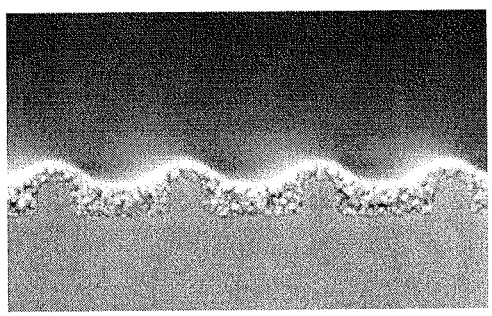
FIG. 10 is a cross-sectional SEM photograph indicating a planarizing property test result of Comparative Example 1 (at a magnification of 100,000).
Figure 11:
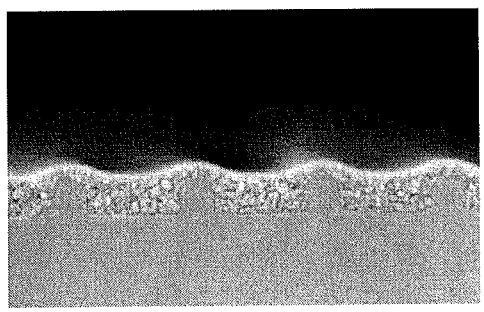
FIG. 11 is a cross-sectional SEM photograph indicating a planarizing property test result of Comparative Example 2 (at a magnification of 100,000).
Figure 12:
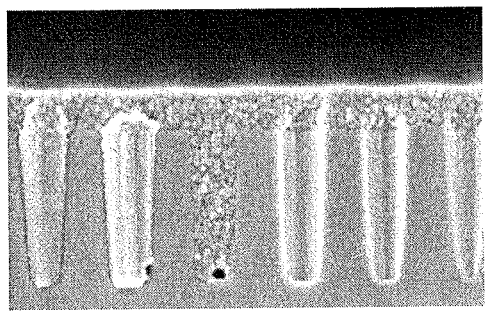
FIG. 12 is a cross-sectional SEM photograph indicating an embeddability test result of Example 1 (at a magnification of 100,000).
Figure 13:
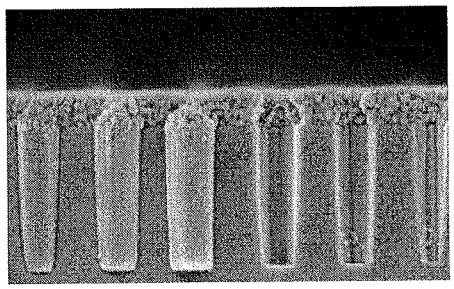
FIG. 13 is a cross-sectional SEM photograph indicating an embeddability test result of Example 3 (at a magnification of 100,000).
Figure 14:
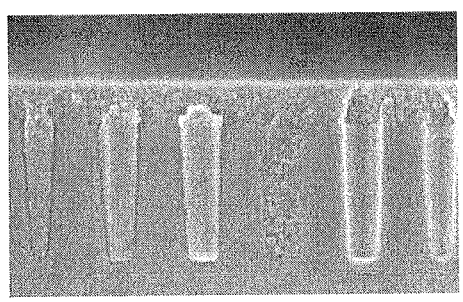
FIG. 14 is a cross-sectional SEM photograph indicating an embeddability test result of Example 4 (at a magnification of 100,000).
Figure 15:
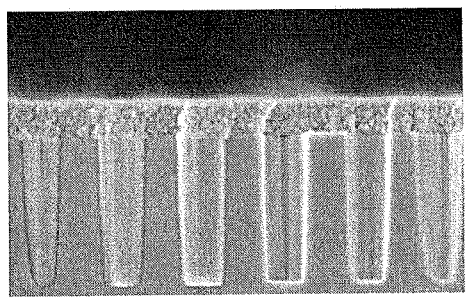
FIG. 15 is a cross-sectional SEM photograph indicating an embeddability test result of Example 6 (at a magnification of 100,000).
Figure 16:
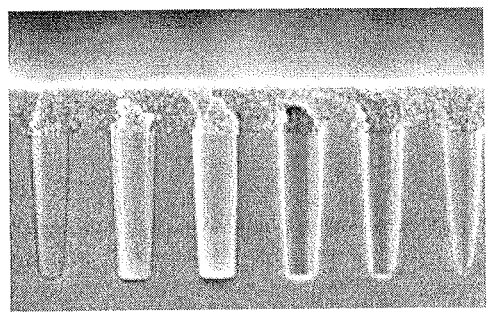
FIG. 16 is a cross-sectional SEM photograph indicating an embeddability test result of Example 7 (at a magnification of 100,000).
Figure 17:
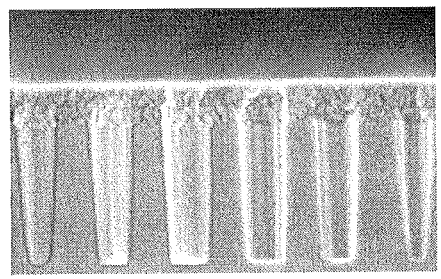
FIG. 17 is a cross-sectional SEM photograph indicating an embeddability test result of Example 8 (at a magnification of 100,000).
Figure 18:
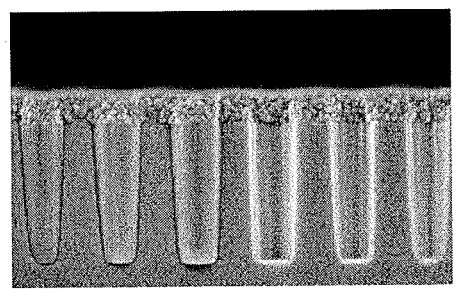
FIG. 18 is a cross-sectional SEM photograph indicating an embeddability test result of Example 9 (at a magnification of 100,000).
Figure 19:
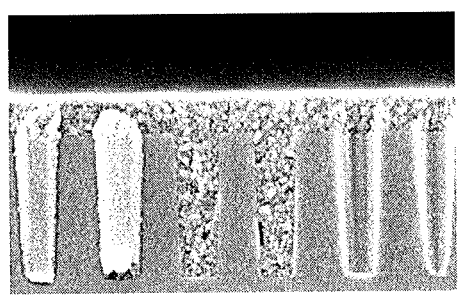
FIG. 19 is a cross-sectional SEM photograph indicating an embeddability test result of Example 10 (at a magnification of 100,000).
Figure 20:
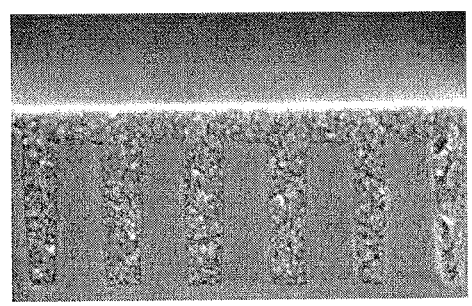
FIG. 20 is a cross-sectional SEM photograph indicating an embeddability test result of Example 11 (at a magnification of 100,000).
Figure 21:
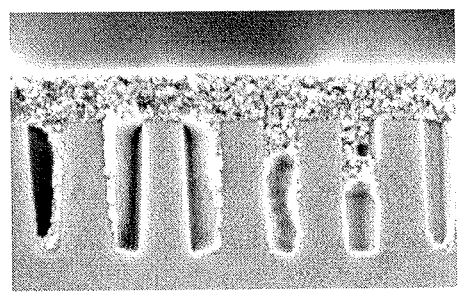
FIG. 21 is a cross-sectional SEM photograph indicating an embeddability test result of Comparative Example 1 (at a magnification of 100,000).
Figure 22:
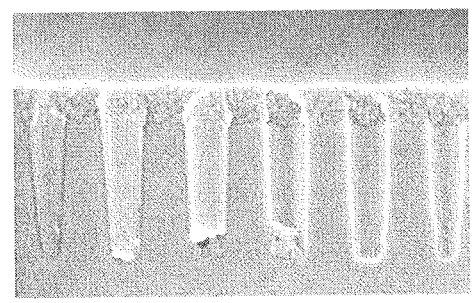
FIG. 22 is a cross-sectional SEM photograph indicating an embeddability test result of Comparative Example 2 (at a magnification of 100,000).

The invention of the present application provides a resist underlayer film-forming composition comprising a phenol novolac resin that is obtained by causing a compound that has at least three phenolic groups, in which each of the phenolic groups has a structure bonded to a tertiary carbon atom or has a structure bonded to a quaternary carbon atom to which a methyl group binds, to react with an aromatic aldehyde or an aromatic ketone in the presence of an acid catalyst. The resist underlayer film-forming composition for lithography contains the resin and a solvent in the present invention. This composition may contain a cross-linking agent, an acid, an acid generator, and a surfactant, for example, as necessary. The solid content of the composition is 0.1 to 70% by mass or 0.1 to 60% by mass. The solid content is the content of all components of the resist underlayer film-forming composition excluding the solvent. The solid content may contain the polymer at a proportion of 1 to 100% by mass, 1 to 99.9% by mass, 50 to 99.9% by mass, 50 to 95% by mass, or 50 to 90% by mass. The polymer used in the present invention has a weight-average molecular weight of 600 to 1,000,000 or 600 to 200,000.

The phenol novolac resin contains a unit structure of Formula (1), a unit structure of Formula (2), a unit structure of Formula (3), a unit structure of Formula (4), or a combination of these unit structures. In Formulae (1) to (4), A is an organic group having at least three phenolic groups, in which each of the phenolic groups has a structure bonded to a tertiary carbon atom or has a structure bonded to a quaternary carbon atom to which a methyl group binds, and each of $B^1$, $B^2$, $B^3$, and $B^4$ is Formula (5). In Formula (5), $C^1$ is a $C_{6-40}$ aryl group or a heterocyclic group that is optionally substituted with a halogen group, a nitro group, an amino group, or a hydroxy group; $C^2$ is a hydrogen atom or a $C_{1-10}$ alkyl group, a $C_{6-40}$ aryl group, or a heterocyclic group each of which is optionally substituted with a halogen group, a nitro group, an amino group, or a hydroxy group; and $C^1$ and $C^2$ optionally form a ring together with a carbon atom bonded to $C^1$ and $C^2$.

Examples of the $C_{1-10}$ alkyl group include a methyl group, an ethyl group, an n-propyl group, an i-propyl group, a cyclopropyl group, an n-butyl group, an i-butyl group, an s-butyl group, a t-butyl group, a cyclobutyl group, a 1-methyl-cyclopropyl group, a 2-methyl-cyclopropyl group, an n-pentyl group, a 1-methyl-n-butyl group, a 2-methyl-n-butyl group, a 3-methyl-n-butyl group, a 1,1-dimethyl-n-propyl group, a 1,2-dimethyl-n-propyl group, a 2,2-dimethyl-n-propyl group, a 1-ethyl-n-propyl group, a cyclopentyl group, a 1-methyl-cyclobutyl group, a 2-methyl-cyclobutyl group, a 3-methyl-cyclobutyl group, a 1,2-dimethyl-cyclopropyl group, a 2,3-dimethyl-cyclopropyl group, a 1-ethyl-cyclopropyl group, a 2-ethyl-cyclopropyl group, an n-hexyl group, a 1-methyl-n-pentyl group, a 2-methyl-n-pentyl group, a 3-methyl-n-pentyl group, a 4-methyl-n-pentyl group, a 1,1-dimethyl-n-butyl group, a 1,2-dimethyl-n-butyl group, a 1,3-dimethyl-n-butyl group, a 2,2-dimethyl-n-butyl group, a 2,3-dimethyl-n-butyl group, a 3,3-dimethyl-n-butyl group, a 1-ethyl-n-butyl group, a 2-ethyl-n-butyl group, a 1,1,2-trimethyl-n-propyl group, a 1,2,2-trimethyl-n-propyl group, a 1-ethyl-1-methyl-n-propyl group, a 1-ethyl-2-methyl-n-propyl group, a cyclohexyl group, a 1-methyl-cyclopentyl group, a 2-methyl-cyclopentyl group, a 3-methyl-cyclopentyl group, a 1-ethyl-cyclobutyl group, a 2-ethyl-cyclobutyl group, a 3-ethyl-cyclobutyl group, a 1,2-dimethyl-cyclobutyl group, a 1,3-dimethyl-cyclobutyl group, a 2,2-dimethyl-cyclobutyl group, a 2,3-dimethyl-cyclobutyl group, a 2,4-dimethyl-cyclobutyl group, a 3,3-dimethyl-cyclobutyl group, a 1-n-propyl-cyclopropyl group, a 2-n-propyl-cyclopropyl group, a 1-i-propyl-cyclopropyl group, a 2-i-propyl-cyclopropyl group, a 1,2,2-trimethyl-cyclopropyl group, a 1,2,3-trimethyl-cyclopropyl group, a 2,2,3-trimethyl-cyclopropyl group, a 1-ethyl-2-methyl-cyclopropyl group, a 2-ethyl-1-methyl-cyclopropyl group, a 2-ethyl-2-methyl-cyclopropyl group, and a 2-ethyl-3-methyl-cyclopropyl group.

Examples of the $C_{6-40}$ aryl group include a phenyl group, an o-methylphenyl group, an m-methylphenyl group, a p-methylphenyl group, an o-chlorophenyl group, an m-chlorophenyl group, a p-chlorophenyl group, an o-fluorophenyl group, a p-fluorophenyl group, an o-methoxyphenyl group, a p-methoxyphenyl group, a p-nitrophenyl group, a p-cyanophenyl group, an α-naphthyl group, a β-naphthyl group, an o-biphenylyl group, an m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, and a 9-phenanthryl group.

The heterocyclic group is preferably an organic group including a five- or six-membered heterocyclic ring containing nitrogen, sulfur, and oxygen atom, and examples thereof include a pyrrole group, a furan group, a thiophene group, an imidazole group, an oxazole group, a thiazole group, a pyrazole group, an isoxazole group, an isothiazole group, a pyridine group, a triazine group, and a triazinetrione group.

In the unit structure of Formula (1), the unit structure of Formula (2), the unit structure of Formula (3), the unit structure of Formula (4), or the combination of these unit structures, A may be Formula (6). In Formula (6), T is a single bond, a $C_{1-10}$ alkylene group, or a $C_{6-40}$ arylene group; $X^1$ and $X^2$ each are a hydrogen atom or a methyl group; $R^1$ to $R^4$ each are a hydrogen atom or a $C_{1-10}$ alkyl group; $R^5$ to $R^8$ each are a $C_{1-10}$ alkyl group or a $C_{6-40}$ aryl group; n1 to n4 each are an integer of 0 to 3; and each of the phenolic groups appropriately binds to $B^1$, $B^2$, $B^3$, and $B^4$. The alkyl group and the aryl group have been exemplified by the alkyl groups and the aryl groups described above. Examples of the alkylene group include alkylene groups derived from the alkyl groups described above. Examples of the arylene group include arylene groups derived from the aryl groups described above.

In the unit structure of Formula (1), the unit structure of Formula (2), the unit structure of Formula (3), the unit structure of Formula (4), or the combination of these unit structures, A may be Formula (7). In Formula (7), $R^9$ to $R^{11}$ each are a hydrogen atom or a $C_{1-10}$ alkyl group; $R^{12}$ to $R^{14}$ each are a $C_{1-10}$ alkyl group or a $C_{6-40}$ aryl group; $X^3$ is a hydrogen atom or a methyl group; n5 to n7 each are an integer of 0 to 3; and each of the phenolic groups appropriately binds to $B^1$, $B^2$, $B^3$, and $B^4$. The alkyl group and the aryl group herein can be exemplified by the alkyl groups and the aryl groups described above.

A used in the present invention is a polynuclear phenol, which is a compound having, in one molecule, at least three or more phenyl groups each of which has at least one or more hydroxy groups or alkoxy groups.

The novolac resin used in the present invention is a novolac resin that is obtained by condensing polynuclear phenols with aldehydes or ketones, and the polynuclear phenols may be used alone or in combination of two or more types thereof.

Examples of the polynuclear phenol used for producing the polymer of the present invention include 1,1,2,2-tetrakis(4-hydroxyphenyl)ethane, 1,1,2,2-tetrakis(3-methyl-4-hydroxyphenyl)ethane, 1,1,2,2-tetrakis(4-hydroxymethylphenyl)ethane, 1,1,3,3-tetrakis(4-hydroxyphenyl)propane, α,α,α'α'-tetrakis(4-hydroxyphenyl)-p-xylene, α,α,α',α'-tetrakis(3-methyl-4-hydroxyphenyl)-p-xylene, α,α,α',α'-tetrakis(4-methoxyphenyl)-p-xylene, α,α,α',α'-tetrakis(4-hydroxyphenyl)-2,5-dimethyl-p-xylene, α,α,α',α'-tetrakis(4-hydroxyphenylmethyl)-naphthalene, tris(4-hydroxyphenyl)methane, and tris(4-hydroxyphenyl)ethane.

Examples of the aldehydes used for producing the polymer of the present invention include saturated aliphatic aldehydes such as formaldehyde, paraformaldehyde, acetaldehyde, propylaldehyde, butyraldehyde, isobutyraldehyde, valeraldehyde, caproaldehyde, 2-methylbutyraldehyde, hexanal, undecanal, 7-methoxy-3,7-dimethyloctyl aldehyde, cyclohexanal, 3-methyl-2-butyraldehyde, glyoxal, malonaldehyde, succinaldehyde, glutaraldehyde, glutaraldehyde, and adipaldehyde; unsaturated aliphatic aldehydes such as acrolein and methacrolein; heterocyclic aldehydes such as furfural and pyridine aldehyde; and aromatic aldehydes such as benzaldehyde, naphthylaldehyde, 9-anthrylaldehyde, phenanthrylaldehyde, salicylaldehyde, phenylacetaldehyde, 3-phenylpropionaldehyde, tolylaldehyde, (N,N-dimethylamino)benzaldehyde, acetoxybenzaldehyde, and 1-pyrenecarboxyaldehyde. In particular, the aromatic aldehydes can be preferably used, and 9-anthrylaldehyde and 1-pyrenecarboxyaldehyde can be more preferably used.

As the ketones used for producing the polymer of the present invention, diaryl ketones are used, and examples thereof include diphenyl ketone, phenyl naphthyl ketone, dinaphthyl ketone, phenyl tolyl ketone, ditolyl ketone, and 9-fluorenone.

The polymer used in the present invention is a novolac resin obtained by condensing polynuclear phenols with aldehydes or ketones. In this condensation reaction, aldehydes or ketones can be used in an amount of 0.1 to 10, preferably 0.1 to 2, equivalents per equivalent of phenyl groups that are included in polynuclear phenols and involved in the reaction.

Examples of an acid catalyst used in the condensation reaction include mineral acids such as sulfuric acid, phosphoric acid, and perchloric acid; organic sulfonic acids such as p-toluenesulfonic acid, p-toluenesulfonic acid monohydrate, and methanesulfonic acid; and carboxylic acids such as formic acid and oxalic acid. The use amount of the acid catalyst is variously selected depending on the type of an acid to be used. Generally, the amount is 0.001 to 10,000 parts by mass, preferably 0.01 to 1,000 parts by mass, and more preferably 0.1 to 100 parts by mass with respect to 100 parts by mass of carbazoles, or of carbazoles and a hydroxy group-containing aromatic compound.

The reaction may be performed without a solvent, but is generally performed with a solvent. Any solvent can be used as long as it does not inhibit the reaction. Examples of the solvent include ethers such as 1,2-dimethoxyethane, diethylene glycol dimethyl ether, propylene glycol monomethyl ether, tetrahydrofuran, and dioxane. If the acid catalyst used is a liquid acid such as formic acid, the catalyst can also serve as the solvent. The reaction temperature during condensation is generally 40° C. to 200° C. The reaction time is variously selected depending on the reaction temperature, but is generally about 30 minutes to 50 hours.

The weight-average molecular weight Mw of the polymer thus obtained is generally 500 to 1,000,000, or 600 to 200,000.

The phenol novolac resin used in the present invention are exemplified below.

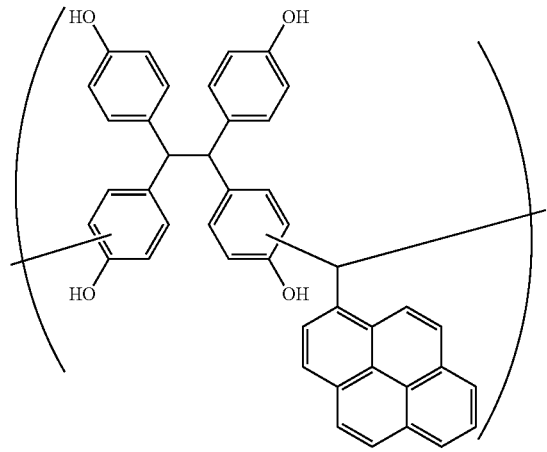

Formula (8-1)

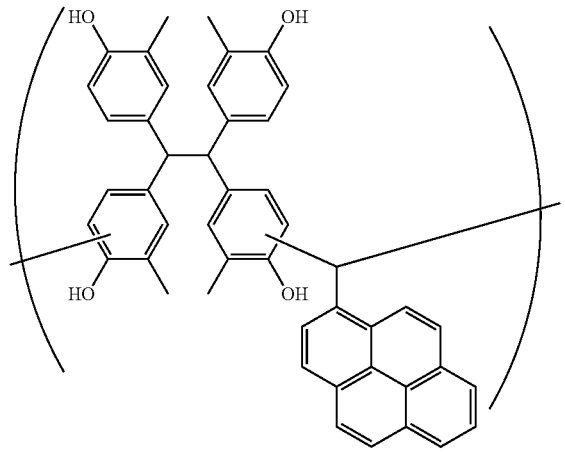

Formula (8-2)

-continued
Formula (8-3)
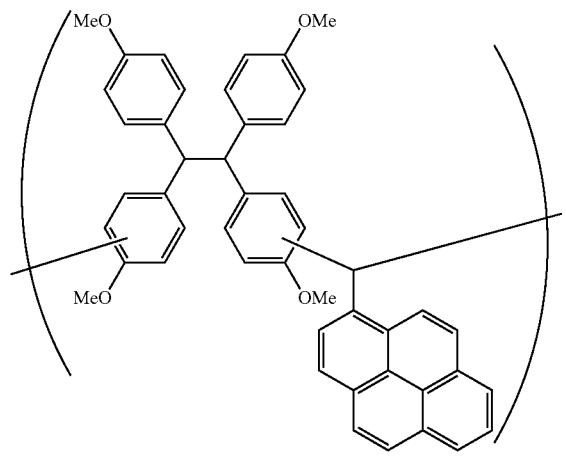
Formula (8-4)
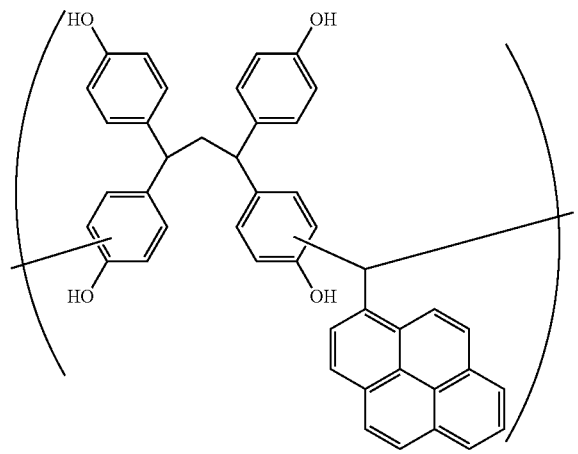
Formula (8-5)
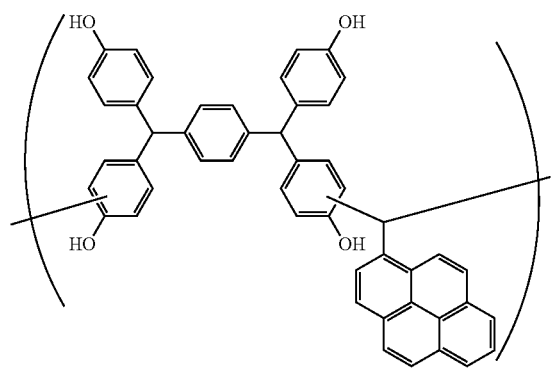
Formula (8-6)
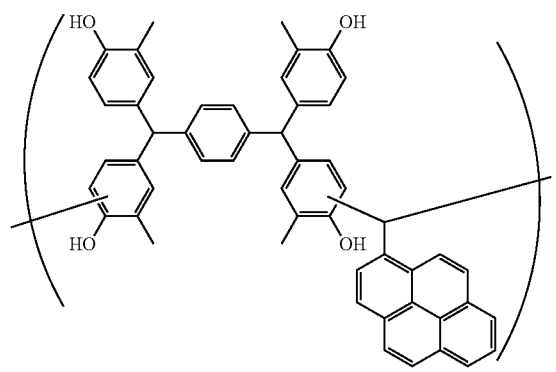
Formula (8-7)
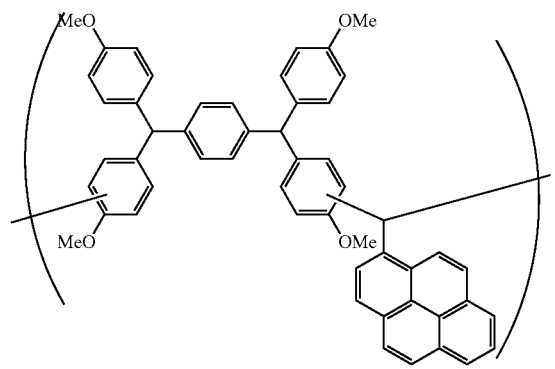
Formula (8-8)
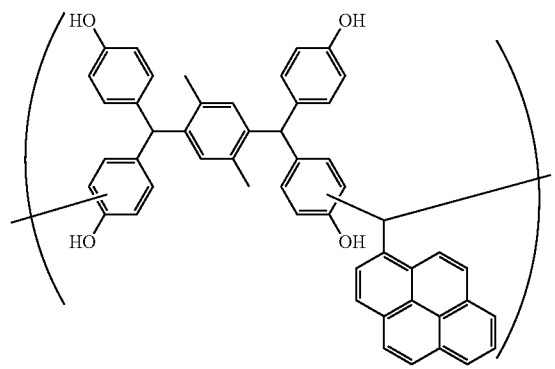

Formula (8-9)
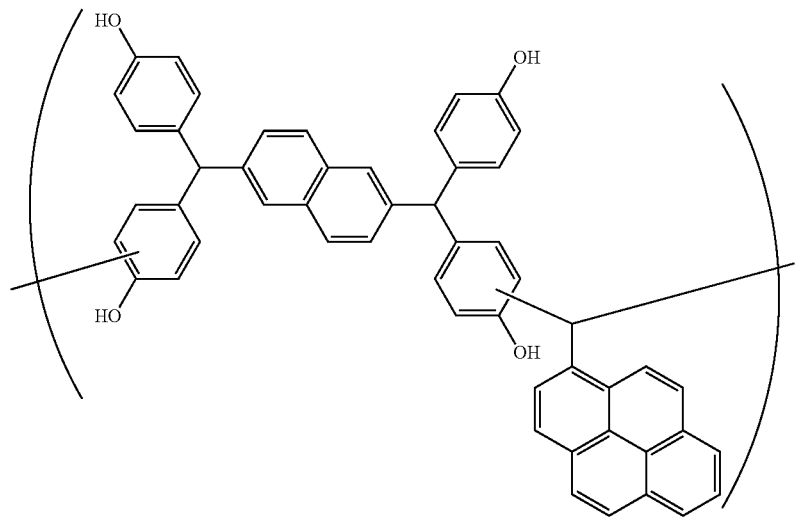
Formula (8-10)
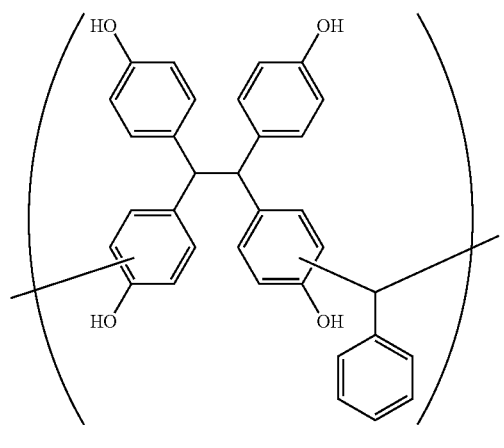
Formula (8-11)
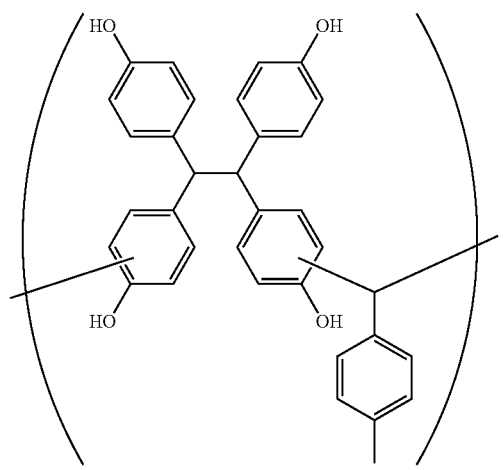
Formula (8-12)
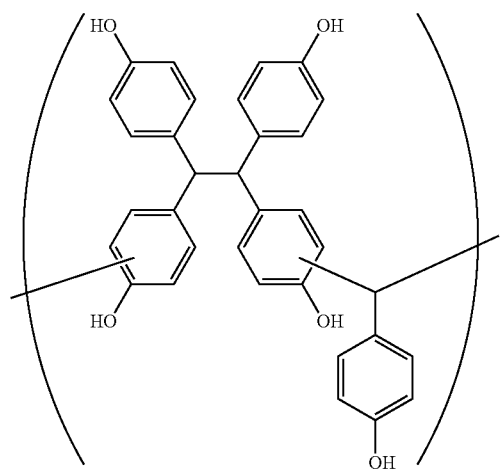
Formula (8-13)
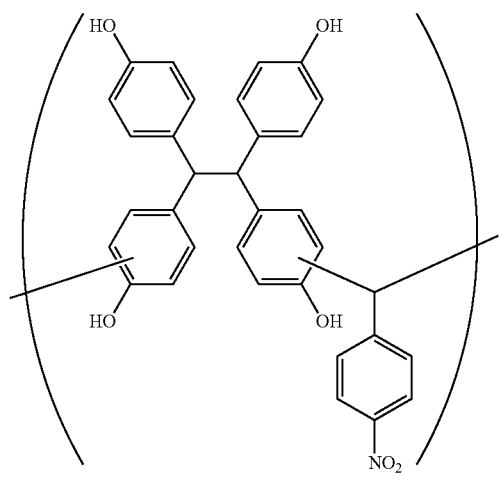

Formula (8-14)
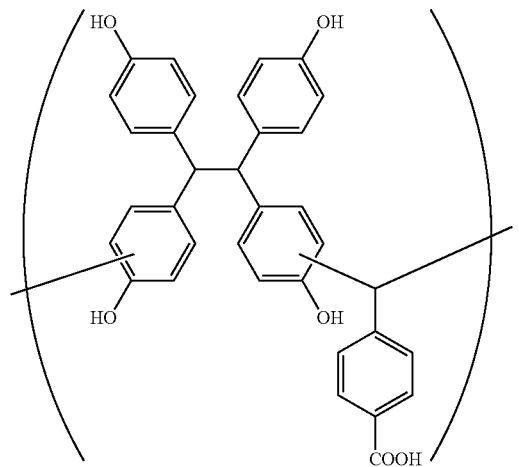
Formula (8-15)
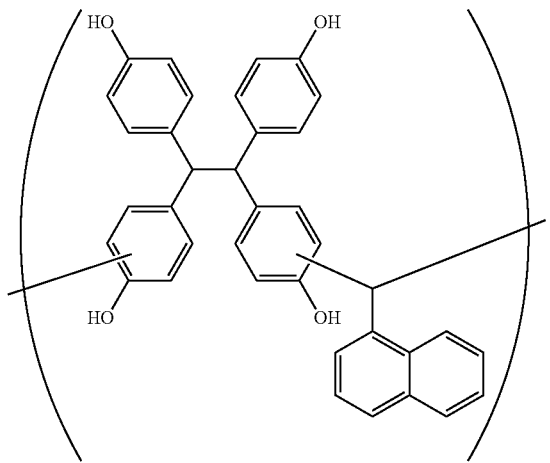
Formula (8-16)
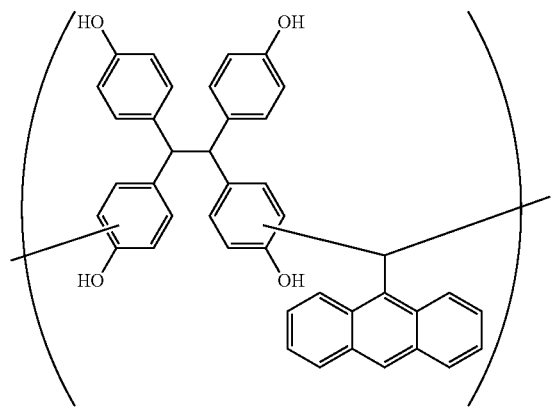
Formula (8-17)
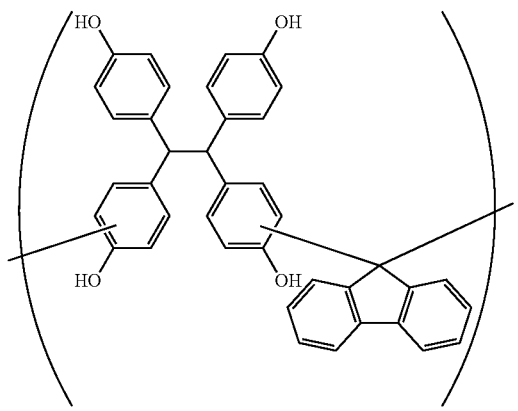
Formula (8-18)
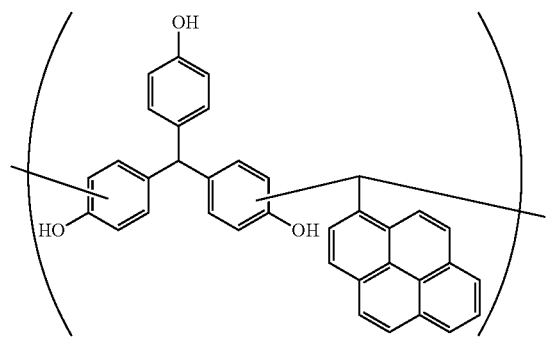
Formula (8-19)
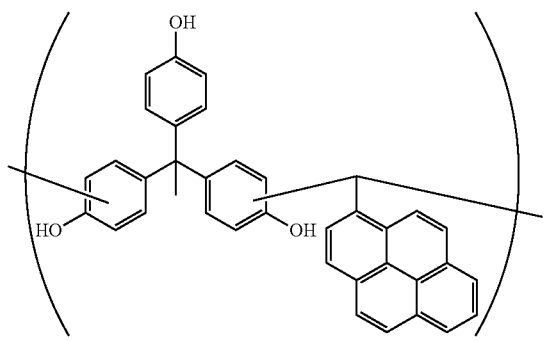

-continued
Formula (8-20)
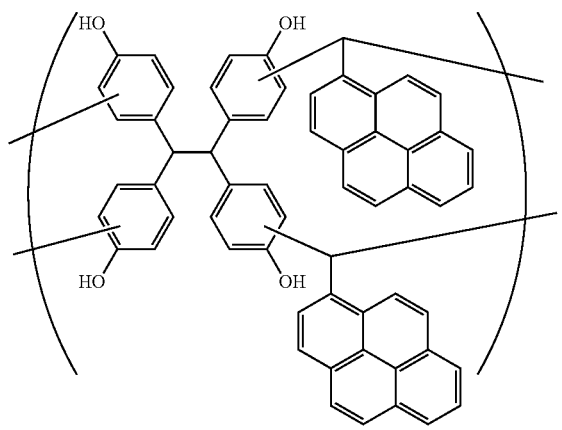
Formula (8-21)
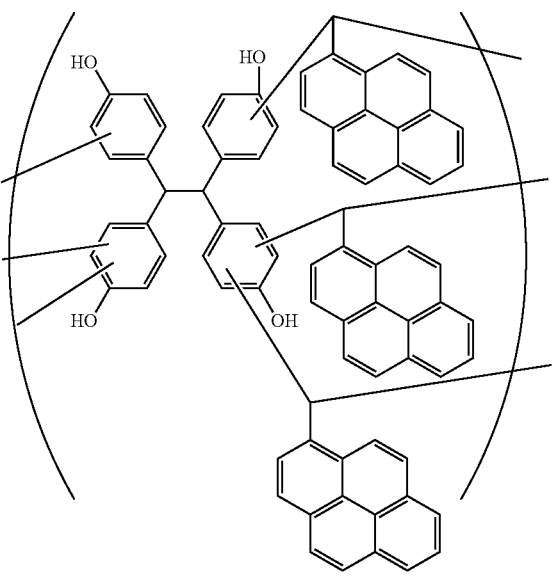
Formula (8-22)
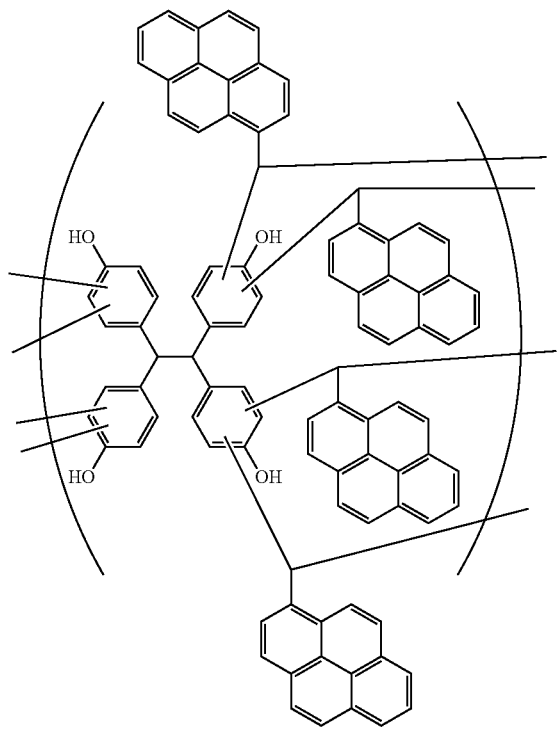
Formula (8-23)
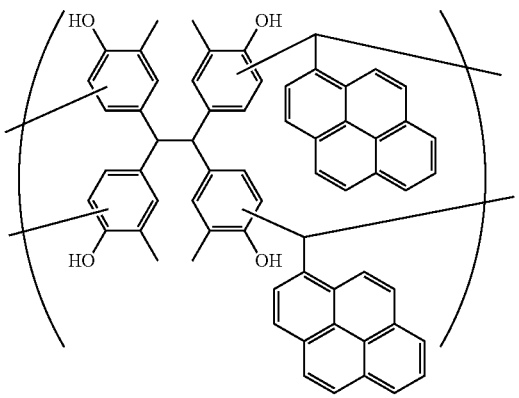

Formula (8-24)
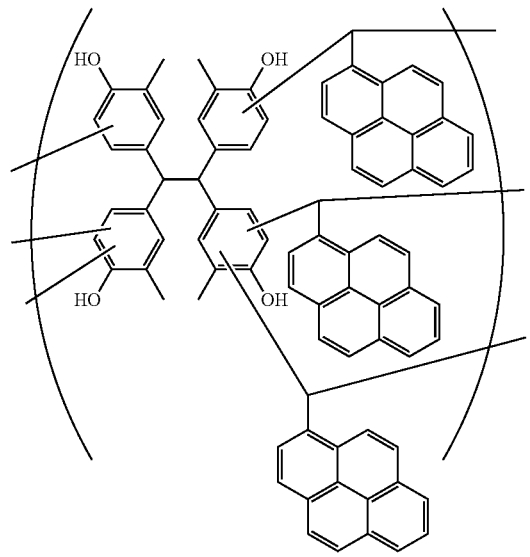
Formula (8-25)
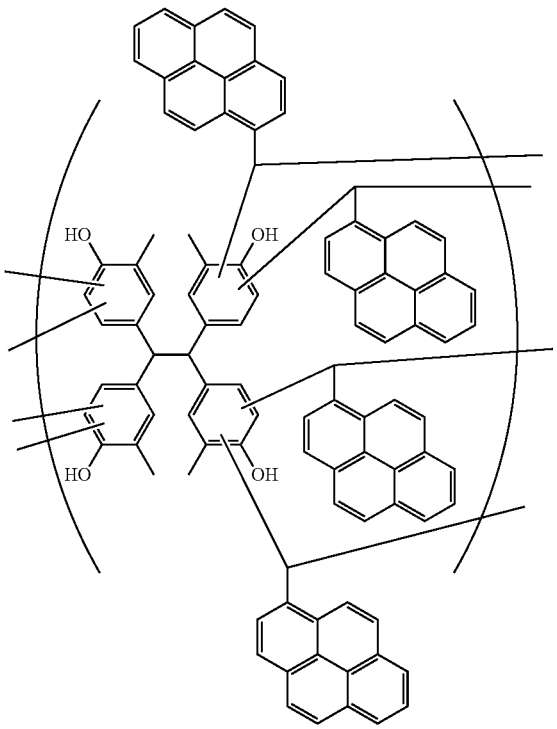
Formula (8-26)
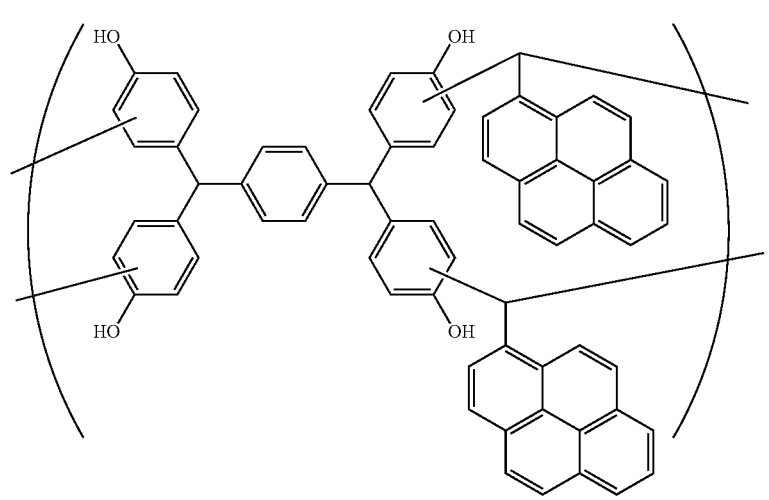

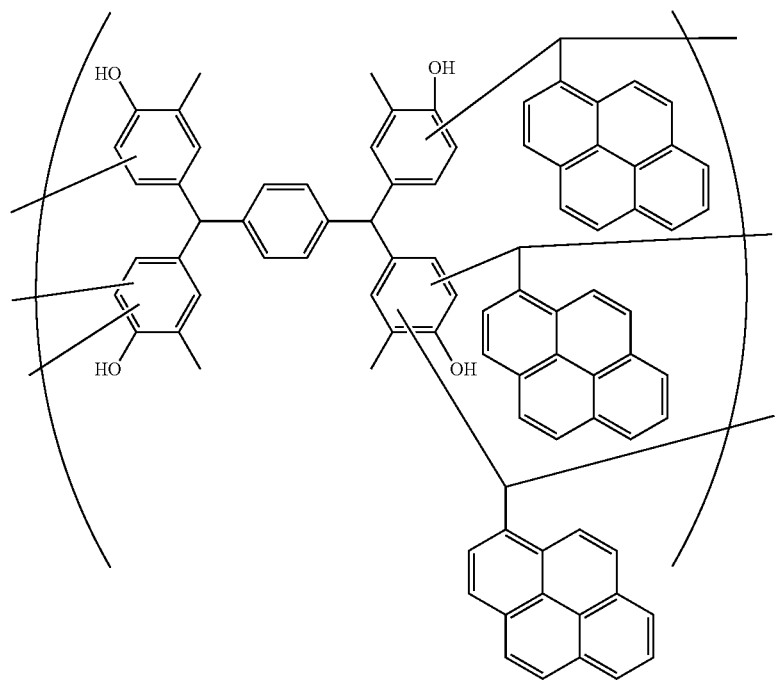
Formula (8-27)
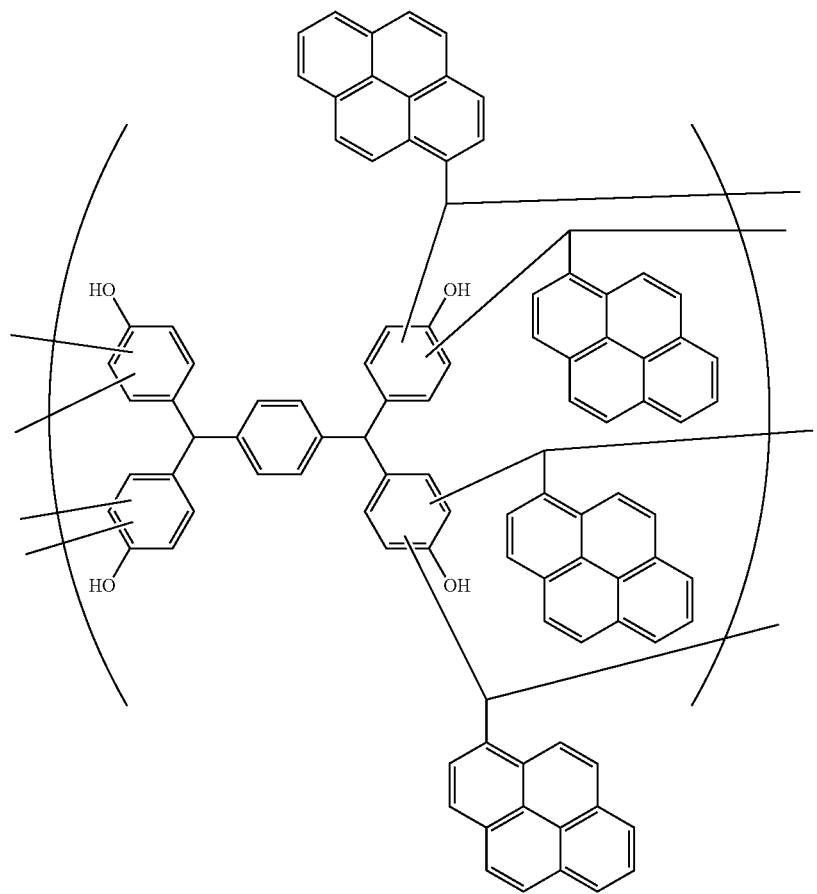
Formula (8-28)

Formula (8-29)

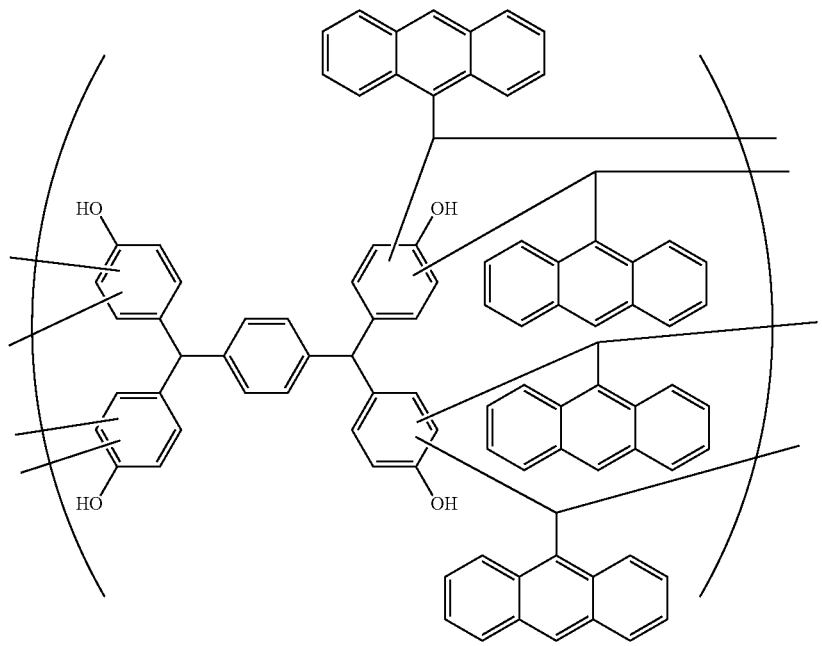

Formula (8-30)

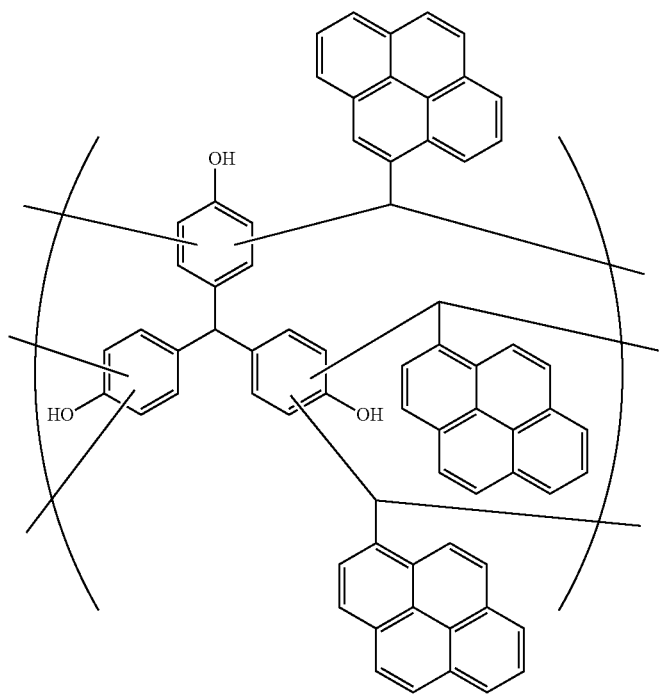

The resist underlayer film-forming composition of the present invention may contain a cross-linking agent component. Examples of the cross-linking agent include melamine-based agents, substituted urea-based agents, and polymer-based agents thereof. Preferred cross-linking agents have at least two cross-link forming substituents, and examples of the cross-linking agents include compounds such as methoxymethylated glycoluril, butoxymethylated glycoluril, methoxymethylated melamine, butoxymethylated melamine, methoxymethylated benzoguanamine, butoxymethylated benzoguanamine, methoxymethylated urea, butoxymethylated urea, methoxymethylated thiourea, and methoxymethylated thiourea. Condensation products of these compounds can also be used.

A cross-linking agent having high heat resistance can be used as the cross-linking agent. As the cross-linking agent having high heat resistance, a compound containing a cross-link forming substituent having an aromatic ring (e.g., a benzene ring or a naphthalene ring) in the molecule can be preferably used.

Examples of this compound include compounds having a partial structure of Formula (9) below, and polymers or oligomers having a repeating unit of Formula (10) below.

Formula (9)

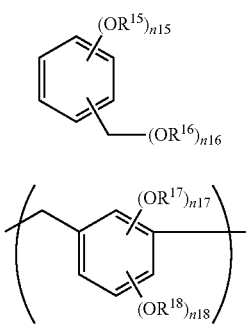

Formula (10)

$R^{15}$, $R^{16}$, $R^{17}$, and $R^{18}$ above are each independently a hydrogen atom or a $C_{1-10}$ alkyl group, and the examples of the alkyl group described above can be used therefor. Herein, n15 is an integer of 1 to 4; n16 is an integer of 1 to (5−n15); (n15+n16) is an integer of 2 to 5; n17 is an integer of 1 to 4; n18 is 0 to (4−n17); and (n17+n18) is an integer of 1 to 4. The number of repeating unit structures of oligomers and polymers that can be used is in a range of 2 to 100 or 2 to 50. The compounds, polymers, and oligomers of Formula (9) and Formula (10) are exemplified below.

Formula (11-1)

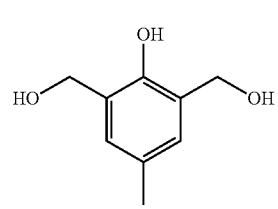

Formula (11-2)

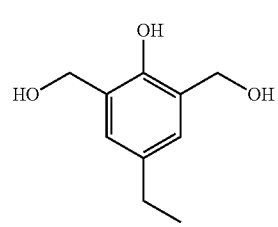

Formula (11-3)

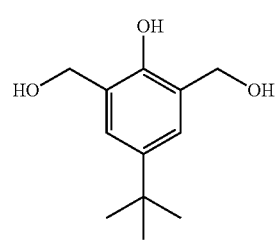

Formula (11-4)

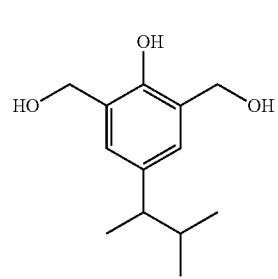

Formula (11-5)

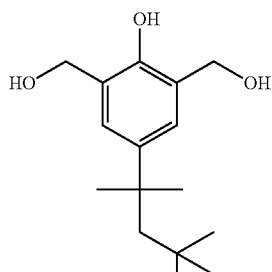

Formula (11-6)

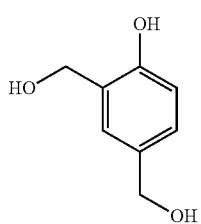

Formula (11-7)

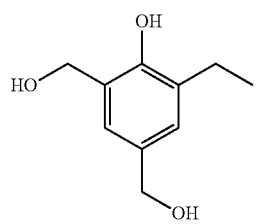

Formula (11-8)

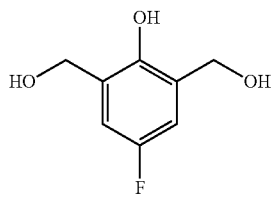

Formula (11-9)

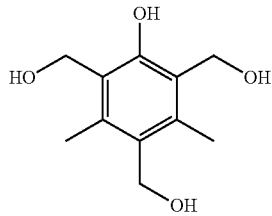

Formula (11-10)

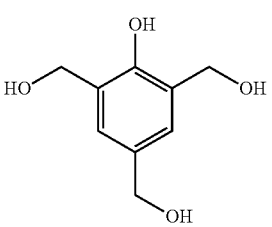

Formula (11-11)

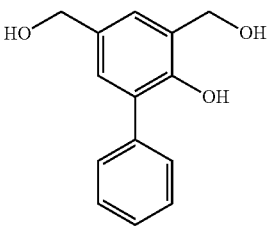

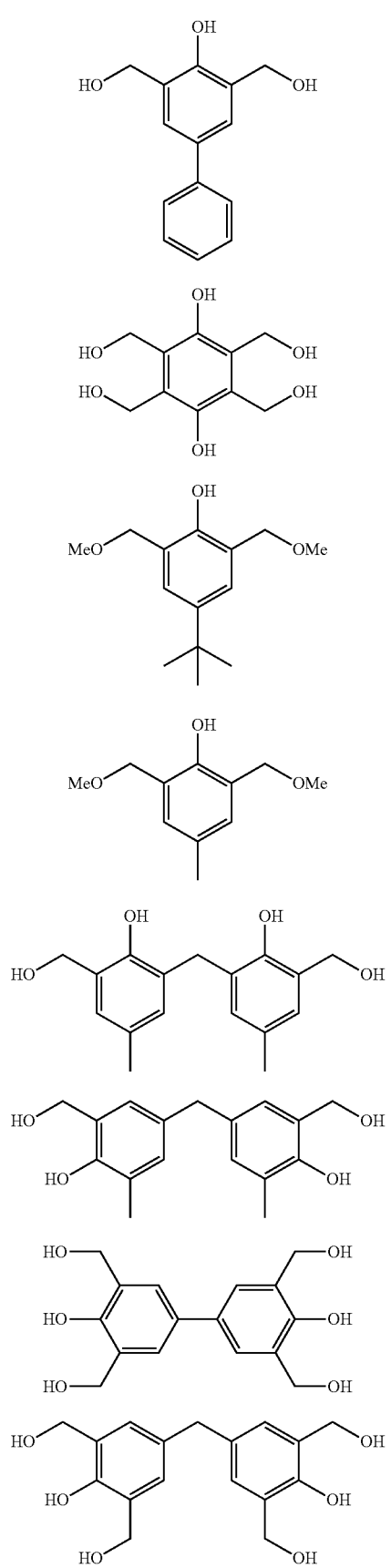
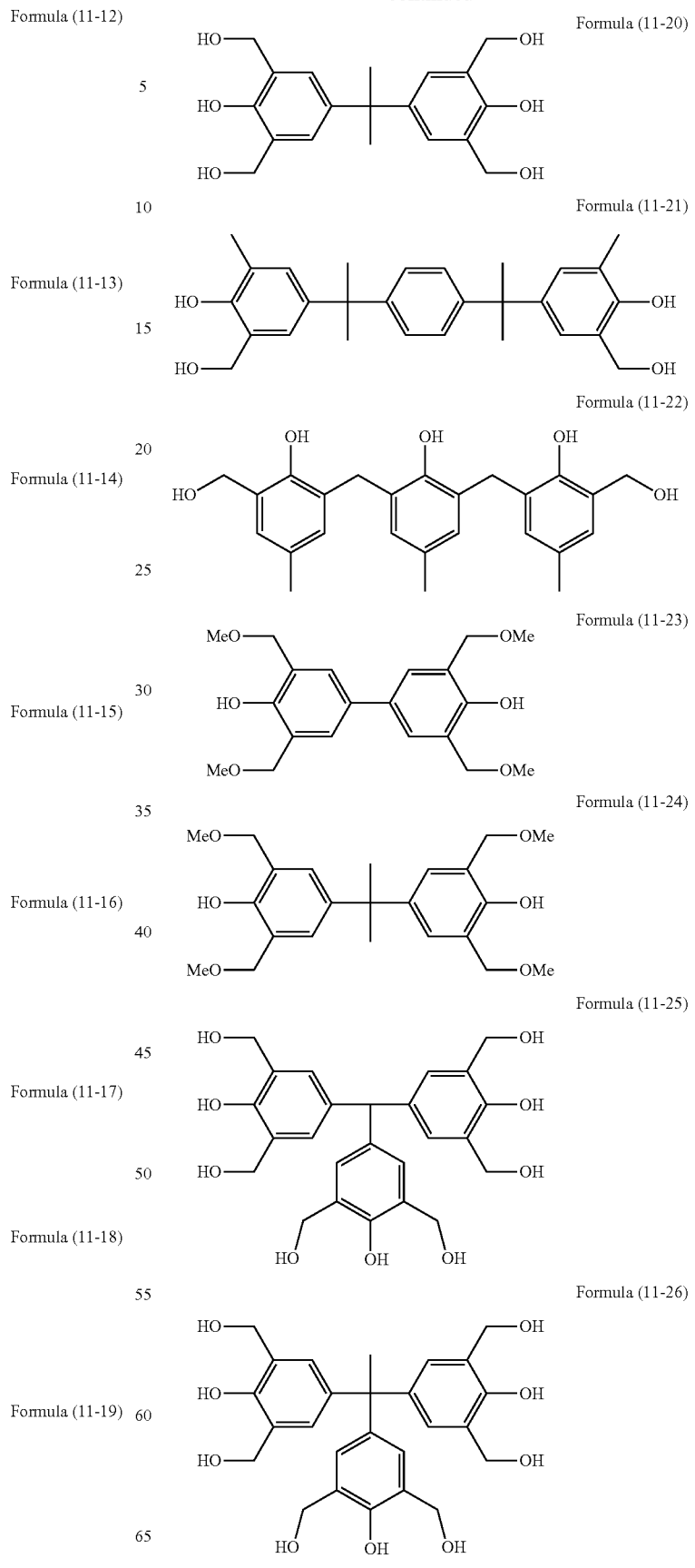

-continued

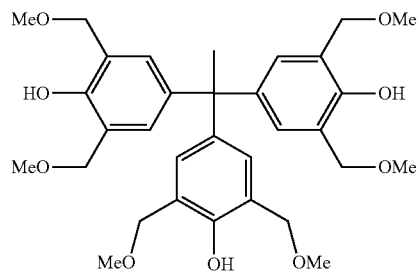

Formula (11-27)

These compounds are available as products of Asahi Organic Chemicals Industry Co., Ltd. and Honshu Chemical Industry Co., Ltd. For example, the compound of Formula (11-24) among the cross-linking agents is available as a trade name of TM-BIP-A from Asahi Organic Chemicals Industry Co., Ltd. The addition amount of the cross-linking agent depends on a solvent used for application, an underlying substrate used, a solution viscosity required, and a film shape required, for example, and is 0.001 to 80% by mass, preferably 0.01 to 50% by mass, and more preferably 0.05 to 40% by mass with respect to the total solid contents. These cross-linking agents may cause cross-linking reaction by self-condensation but, when a cross-linkable substituent exists in the polymer of the present invention, the cross-linking agents can cause cross-linking reaction with the cross-linkable substituent.

In the present invention, as a catalyst for promoting the cross-linking reaction, an acidic compound such as p-toluenesulfonic acid, trifluoromethanesulfonic acid, pyridinium p-toluenesulfonic acid, salicylic acid, 5-sulfosalicylic acid, 4-phenolsulfonic acid, camphorsulfonic acid, 4-chlorobenzenesulfonic acid, benzenedisulfonic acid, 1-naphthalenesulfonic acid, citric acid, benzoic acid, hydroxybenzoic acid, or naphthalenecarboxylic acid; and/or a thermal acid generator such as 2,4,4,6-tetrabromocyclohexadienone, benzoin tosylate, 2-nitrobenzyl tosylate, or other organic sulfonic acid alkyl esters can be blended. The blending amount of the catalyst is 0.0001 to 20% by mass, preferably 0.0005 to 10% by mass, and more preferably 0.01 to 3% by mass with respect to the total solid contents.

A photoacid generator can be added to the coating-type resist underlayer film-forming composition for lithography of the present invention in order to match the acidity with that of a photoresist that is coated on the upper layer in a lithography process. Examples of the photoacid generator preferred include onium salt-based photoacid generators such as bis(4-t-butylphenyl)iodonium trifluoromethanesulfonate and triphenyl sulfonium trifluoromethanesulfonate; halogen-containing compound-based photoacid generators such as phenyl-bis(trichloromethyl)-s-triazine; and sulfonic acid-based photoacid generators such as benzoin tosylate and N-hydroxysuccinimide trifluoromethanesulfonate. The addition amount of the photoacid generator is 0.2 to 10% by mass, and preferably 0.4 to 5% by mass with respect to the total solid contents.

A light absorber, a rheology control agent, an adhesion assistant, and a surfactant, for example, other than the agents above can be further added as necessary to the resist underlayer film material for lithography of the present invention.

Examples of such an additional light absorber include commercially available light absorbers described in "*Kogyo-yo Shikiso no Gijutsu to Shijo* (Technology and Market of Industrial Dyes)" (CMC Publishing) or "*Senryo Binran* (Handbook for Dyes)" (edited by The Society of Synthetic Organic Chemistry, Japan). For example, C. I. Disperse Yellow 1, 3, 4, 5, 7, 8, 13, 23, 31, 49, 50, 51, 54, 60, 64, 66, 68, 79, 82, 88, 90, 93, 102, 114, and 124; C. I. Disperse Orange 1, 5, 13, 25, 29, 30, 31, 44, 57, 72, and 73; C. I. Disperse Red 1, 5, 7, 13, 17, 19, 43, 50, 54, 58, 65, 72, 73, 88, 117, 137, 143, 199, and 210; C. I. Disperse Violet 43; C. I. Disperse Blue 96; C. I. Fluorescent Brightening Agent 112, 135, and 163; C. I. Solvent Orange 2 and 45; C. I. Solvent Red 1, 3, 8, 23, 24, 25, 27, and 49; C. I. Pigment Green 10; and C. I. Pigment Brown 2 can be suitably used. These light absorbers are generally blended in a proportion of 10% by mass or less, and preferably 5% by mass or less, with respect to the total solids of the resist underlayer film material for lithography.

The rheology control agent is added mainly for the purpose of improving the flowability of the resist underlayer film-forming composition and, particularly in a baking process, improving the film thickness uniformity of the resist underlayer film and enhancing the filling ability of the resist underlayer film-forming composition into holes. Specific examples of the rheology control agent include phthalic acid derivatives such as dimethyl phthalate, diethyl phthalate, diisobutyl phthalate, dihexyl phthalate, and butylisodecyl phthalate; adipic acid derivatives such as di-n-butyl adipate, diisobutyl adipate, diisooctyl adipate, and octyl decyl adipate; maleic acid derivatives such as di-n-butyl maleate, diethyl maleate, and dinonyl maleate; oleic acid derivatives such as methyl oleate, butyl oleate, and tetrahydrofurfuryl oleate; or stearic acid derivatives such as n-butyl stearate, and glyceryl stearate. These rheology control agents are generally blended in a proportion smaller than 30% by mass with respect to the total solid contents of the resist underlayer film material for lithography.

The adhesion assistant is added mainly for the purpose of improving the adhesiveness between the substrate or the resist and the resist underlayer film-forming composition, and particularly preventing the resist from peeling off during development. Specific examples of the adhesion assistant include chlorosilanes such as trimethylchlorosilane, dimethylvinylchlorosilane, methyldiphenylchlorosilane, and chloromethyldimethylchlorosilane; alkoxysilanes such as trimethylmethoxysilane, dimethyldiethoxysilane, methyldimethoxysilane, dimethylvinylethoxysilane, diphenyldimethoxysilane, and phenyltriethoxysilane; silazanes such as hexamethyldisilazane, N,N'-bis(trimethylsilyl)urea, dimethyltrimethylsilylamine, and trimethylsilylimidazole; silanes such as vinyltrichlorosilane, γ-chloropropyltrimethoxysilane, γ-aminopropyltriethoxysilane, and γ-glycidoxypropyltrimethoxysilane; heterocyclic compounds such as benzotriazole, benzimidazole, indazole, imidazole, 2-mercaptobenzimidazole, 2-mercaptobenzothiazole, 2-mercaptobenzoxazole, urazole, thiouracil, mercaptoimidazole, and mercaptopyrimidine; urea such as 1,1-dimethylurea and 1,3-dimethylurea; and thiourea compounds.

These adhesion assistants are generally added in a proportion smaller than 5% by mass, and preferably smaller than 2% by mass with respect to the total solid contents of the resist underlayer film material for lithography.

A surfactant can be blended into the resist underlayer film material for lithography of the present invention in order to further improve coating properties against surface irregularities without occurrence of pinholes or striations, for example. Examples of the surfactant include nonionic surfactants including polyoxyethylene alkyl ethers such as polyoxyethylene lauryl ether, polyoxyethylene stearyl ether, polyoxyethylene cetyl ether, and polyoxyethylene oleyl ether; polyoxyethylene alkylallyl ethers such as polyoxyethylene octylphenol ether and polyoxyethylene nonylphenol ether; polyoxyethylene-polyoxypropylene block copolymers; sorbitan fatty acid esters such as sorbitan monolaurate, sorbitan monopalmitate, sorbitan monostearate, sorbitan monooleate, sorbitan trioleate, and sorbitan tristearate; and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorine based surfactants including EFTOP EF301, EF303, EF352 (manufactured by Tohkem Products Corp., trade names), MEGAFAC F171, F173, R-30 (manufactured by Dainippon Ink and Chemicals, Inc., trade names), FLUORAD FC430, FC431 (manufactured by Sumitomo 3M Ltd., trade names), ASAHI GUARD AG710, and SURFLON S-382, SC101, SC102, SC103, SC104, SC105, SC106 (manufactured by Asahi Glass Co., Ltd., trade names); and an organosiloxane polymer KP341 (manufactured by Shin-Etsu Chemical Co., Ltd.). The blending amount of these surfactants is generally 2.0% by mass or less, and preferably 1.0% by mass or less with respect to the total solid contents of the resist underlayer film material for lithography of the present invention. These surfactants may be added alone or may be added in combination of two or more types.

In the present invention, examples of solvents that dissolve polymers, cross-linking agent components, and cross-linking catalysts, for example, described above include ethylene glycol monomethyl ether, ethylene glycol monoethyl ether, methyl cellosolve acetate, ethyl cellosolve acetate, diethylene glycol monomethyl ether, diethylene glycol monoethyl ether, propylene glycol, propylene glycol monomethyl ether, propylene glycol monomethyl ether acetate, propylene glycol monoethyl ether, propylene glycol monoethyl ether acetate, propylene glycol propyl ether acetate, toluene, xylene, methyl ethyl ketone, cyclopentanone, cyclohexanone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate, methyl 3-ethoxypropionate, methyl pyruvate, ethyl pyruvate, ethyl acetate, butyl acetate, ethyl lactate, and butyl lactate. These organic solvents are used alone or in combination of two or more types.

High-boiling point solvents such as propylene glycol monobutyl ether and propylene glycol monobutyl ether acetate can be mixed to be used. Among these solvents, propylene glycol monomethyl ether, propylene glycol monomethyl ether acetate, ethyl lactate, butyl lactate, and cyclohexanone, for example, are preferably used to improve leveling properties.

The resist used in the present invention is a photoresist or an electron beam resist.

As the photoresist that is applied onto the resist underlayer film for lithography of the present invention, both a positive photoresist and a negative photoresist can be used. The photoresist may be, for example, a positive photoresist including a novolac resin and 1,2-naphthoquinone diazide sulfonic acid ester; a chemically amplified photoresist including a photoacid generator and a binder having a group that is decomposed by an acid to increase the alkali dissolution rate; a chemically amplified photoresist including an alkali-soluble binder, a low molecular compound that is decomposed by an acid to increase the alkali dissolution rate of the photoresist, and a photoacid generator; a chemically amplified photoresist including a binder having a group that is decomposed by an acid to increase the alkali dissolution rate, a low molecular compound that is decomposed by an acid to increase the alkali dissolution rate of the photoresist, and a photoacid generator; or a photoresist including an Si atom in the skeleton. Examples of the photoresist include a trade name of APEX-E manufactured by Rohm and Haas Co.

Examples of the electron beam resist applied onto the resist underlayer film for lithography of the present invention include a composition made up of a resin that includes an Si—Si bond in a main chain and includes an aromatic ring at an end and of an acid generator that generates an acid by irradiation with electron beams; and a composition made up of a poly(p-hydroxystyrene) in which a hydroxy group is substituted with an organic group containing N-carboxyamine and of an acid generator that generates an acid by irradiation with electron beams. In the latter electron beam resist composition, the acid generated from the acid generator by electron beam irradiation reacts with the N-carboxyaminoxy group on a side chain of the polymer, then the polymer side chain decomposes into hydroxy groups, and the polymer becomes alkali-soluble and dissolves in an alkaline developer to form a resist pattern. Examples of the acid generator that generates an acid by irradiation with electron beams include halogenated organic compounds such as 1,1-bis[p-chlorophenyl]-2,2,2-trichloroethane, 1,1-bis[p-methoxyphenyl]-2,2,2-trichloroethane, 1,1-bis[p-chlorophenyl]-2,2-dichloroethane, and 2-chloro-6-(trichloromethyl)pyridine; onium salts such as a triphenyl sulfonium salt and a diphenyl iodonium salt; and sulfonic acid esters such as nitrobenzyl tosylate and dinitrobenzyl tosylate.

Examples of the developer for a resist having a resist underlayer film that is formed with the resist underlayer film material for lithography of the present invention, which can be used, include aqueous solutions of alkalis including inorganic alkalis such as sodium hydroxide, potassium hydroxide, sodium carbonate, sodium silicate, sodium metasilicate, and aqueous ammonia; primary amines such as ethylamine and n-propylamine; secondary amines such as diethylamine and di-n-butylamine; tertiary amines such as triethylamine and methyldiethylamine; alcohol amines such as dimethylethanolamine and triethanolamine; quaternary ammonium salts such as tetramethylammonium hydroxide, tetraethylammonium hydroxide, and choline; and cyclic amines such as pyrrole and piperidine. An alcohol such as isopropyl alcohol or a surfactant such as a nonionic surfactant can be added to these aqueous alkaline solutions in appropriate amount for use. Among these developers, the quaternary ammonium salts are preferred, and tetramethylammonium hydroxide and choline are more preferred.

The method for forming a resist pattern of the present invention will be described below. The resist underlayer film-forming composition is applied onto a substrate (e.g., a transparent substrate such as a silicon/silicon dioxide coat, a glass substrate, or an ITO substrate) that is used in the production of precision integrated circuit elements by an appropriate coating method using a spinner or a coater, for example, and then is cured by baking to prepare a coating-type underlayer film. The thickness of the resist underlayer film is preferred to be 0.01 to 3.0 μm. As conditions of the baking after the application, the temperature is 80 to 350° C., and the period of time is 0.5 to 120 minutes. Subsequently, a resist is applied directly onto the resist underlayer film or, as necessary, onto a film formed by applying one to several layers of coating film material onto a coating-type resist underlayer film. Light or electron beams are irradiated thereon via a predetermined mask, and then development, rinsing, and drying are performed, whereby a preferable resist pattern can be obtained. Heating may be performed after irradiation with light or electron beams (post exposure baking: PEB) as necessary. The resist underlayer film is then removed by dry etching from portions in which the resist was removed through development in the above-described process, and thus a desired pattern can be formed on the substrate.

The exposure light to the photoresists is actinic rays such as near-ultraviolet rays, far-ultraviolet rays, and extreme-ultraviolet rays (e.g., EUV, wavelength of 13.5 nm). For example, light having a wavelength of 248 nm (KrF laser light), 193 nm (ArF laser light), or 157 nm ($F_2$ laser light) is used. The light irradiation method is not particularly limited as long as an acid can be generated from a photo-acid generator and, for example, the exposure amount is 1 to 2,000 mJ/cm$^2$, 10 to 1,500 mJ/cm$^2$, or 50 to 1,000 mJ/cm$^2$.

Electron beam irradiation of the electron beam resist can be performed by using an electron beam irradiation device, for example.

In the present invention, a semiconductor device can be produced through: a process of forming a resist underlayer film, using the resist underlayer film-forming composition, on a semiconductor substrate; a process of forming a resist film thereon; a process of forming a resist pattern by irradiation with light or electron beams and development; a process of etching the resist underlayer film using the resist pattern; and a process of fabricating the semiconductor substrate using the resist underlayer film patterned.

When a finer resist pattern is further pursued, a problem of resolution and a problem in which the resist pattern collapses after development may occur, and thus thinner resists are required. This makes it difficult to achieve sufficient resist pattern film thickness for fabrication of a substrate, and thus a process has become necessary in which the function of a mask during the substrate fabrication is imparted not only to the resist pattern, but also to a resist underlayer film that is formed between the resist and a semiconductor substrate to be fabricated. As a resist underlayer film for such a process, unlike a conventional resist underlayer film having a high etching-rate property, a resist underlayer film for lithography having a selection ratio of dry etching rate that is close to that of a resist, a resist underlayer film for lithography having a selection ratio of dry etching rate that is smaller than that of the resist, or a resist underlayer film for lithography having a selection ratio of dry etching rate that is smaller than that of a semiconductor substrate is required. An anti-reflection property can be imparted to such a resist underlayer film, which enables the resist underlayer film to serve as a conventional anti-reflective coating.

To obtain fine resist patterns, a process has also begun to be used in which a resist pattern and a resist underlayer film upon dry etching of a resist underlayer film are set to be thinner than the pattern width at the time of resist development. As a resist underlayer film for such a process, unlike a conventional anti-reflective coating having a high etching-rate property, a resist underlayer film for lithography having a selection ratio of dry etching rate that is close to that of a resist is required. An anti-reflection property can be imparted to such a resist underlayer film, which enables the resist underlayer film to serve as a conventional anti-reflective coating.

In the present invention, after the resist underlayer film of the present invention is formed on a substrate, a resist can be applied directly onto the resist underlayer film or, as necessary, onto a film formed by applying one to several layers of coating film material onto the resist underlayer film. Accordingly, the substrate can be fabricated by selecting an appropriate etching gas even if the pattern width of the resist is narrow and the resist is thinly coated in order to prevent pattern collapse.

More specifically, a semiconductor device can be produced through: a process of forming the resist underlayer film on a semiconductor substrate using the resist underlayer film-forming composition; a process of forming thereon a hard mask using a coating film material that contains a silicon component, or a hard mask (e.g., silicon oxynitride) by evaporation; a process of further forming a resist film thereon; a process of forming a resist pattern by irradiation with light or electron beams and development; a process of etching the hard mask using the resist pattern with a halogen-based gas; a process of etching the resist underlayer film using the hard mask patterned with an oxygen-based gas or a hydrogen-based gas; and a process of fabricating the semiconductor substrate using the resist underlayer film patterned with a halogen-based gas.

When the effect of the resist underlayer film-forming composition for lithography of the present invention serving as an anti-reflective coating is considered, the light-absorbing moieties are incorporated in the skeleton and thus no substances diffuse into the photoresist during drying by heating. The light-absorbing moieties also have sufficiently high light-absorbing ability, and thus the resist underlayer film exhibits high anti-reflection effect.

The resist underlayer film-forming composition for lithography of the present invention exhibits high thermal stability, can prevent contamination of an upper layer film caused by decomposition products during baking, and can provide a sufficient temperature margin during the baking process.

Furthermore, the resist underlayer film material for lithography of the present invention can be used as a film that, depending on the process conditions, has a function of preventing reflection of light and also a function of preventing interactions between the substrate and the photoresist or preventing adverse effects on the substrate caused by materials that are used in the photoresist or by substances that are generated during exposure of the photoresist to light.

EXAMPLES

Synthesis Example 1

20.79 g of propylene glycol monomethyl ether was added to 8.65 g of 1,1,2,2-tetrakis(4-hydroxyphenyl)ethane (product name: TEP-DF, manufactured by Asahi Organic Chemicals Industry Co., Ltd.), 5.00 g of 1-pyrenecarboxyaldehyde (manufactured by Maruzen Chemical Industries, Ltd.), and 0.21 g of methanesulfonic acid, and this mixture was stirred under reflux for 23 hours in nitrogen atmosphere. After the reaction was completed, this solution was diluted with 35 g of tetrahydrofuran. This diluted solution was subjected to reprecipitation in a mixed solvent of methanol/water (50% by mass/50% by mass). The obtained precipitate was filtered, and the residue was washed and then dried under reduced pressure at 60° C., whereby 9.4 g of a novolac resin was obtained (including the polymer of Formula (8-1)). The weight-average molecular weight measured in terms of standard polystyrene by GPC was 3,600.

Synthesis Example 2

20.02 g of propylene glycol monomethyl ether was added to 6.06 g of 1,1,2,2-tetrakis(4-hydroxyphenyl)ethane (product name: TEP-DF, manufactured by Asahi Organic Chemicals Industry Co., Ltd.), 7.00 g of 1-pyrenecarboxyaldehyde (manufactured by Maruzen Chemical Industries, Ltd.), and 0.29 g of methanesulfonic acid, and this mixture was stirred under reflux for 23 hours in nitrogen atmosphere. After the reaction was completed, this solution was diluted with 20 g of tetrahydrofuran. This diluted solution was subjected to reprecipitation in a mixed solvent of methanol/water (80% by mass/20% by mass). The obtained precipitate was filtered, and the residue was washed and then dried under reduced pressure at 60° C., whereby 9.1 g of a novolac resin was obtained (including the polymer of Formula (8-20)). The weight-average molecular weight measured in terms of standard polystyrene by GPC was 4,800.

Synthesis Example 3

19.90 g of propylene glycol monomethyl ether was added to 3.89 g of 1,1,2,2-tetrakis(4-hydroxyphenyl)ethane (product name: TEP-DF, manufactured by Asahi Organic Chemicals Industry Co., Ltd.), 9.00 g of 1-pyrenecarboxyaldehyde (manufactured by Maruzen Chemical Industries, Ltd.), and 0.38 g of methanesulfonic acid, and this mixture was stirred under reflux for 23 hours in nitrogen atmosphere. After the reaction was completed, this solution was diluted with 20 g of tetrahydrofuran. This diluted solution was subjected to reprecipitation in a mixed solvent of methanol/water (80% by mass/20% by mass). The obtained precipitate was filtered, and the residue was washed and then dried under reduced pressure at 60° C., whereby 11.2 g of a novolac resin was obtained (including the polymer of Formula (8-22)). The weight-average molecular weight measured in terms of standard polystyrene by GPC was 5,700.

Synthesis Example 4

23.27 g of propylene glycol monomethyl ether was added to 10.30 g of α,α,α',α'-tetrakis(4-hydroxyphenyl)-p-xylene (product name: TEP-TPA, manufactured by Asahi Organic Chemicals Industry Co., Ltd.), 5.00 g of 1-pyrenecarboxyaldehyde (manufactured by Maruzen Chemical Industries, Ltd.), and 0.21 g of methanesulfonic acid, and this mixture was stirred under reflux for 23 hours in nitrogen atmosphere. After the reaction was completed, this solution was diluted with 39 g of tetrahydrofuran. This diluted solution was subjected to reprecipitation in a mixed solvent of methanol/water (50% by mass/50% by mass). The obtained precipitate was filtered, and the residue was washed and then dried under reduced pressure at 60° C., whereby 10.0 g of a novolac resin was obtained (including the polymer of Formula (8-5)). The weight-average molecular weight measured in terms of standard polystyrene by GPC was 4,900.

Synthesis Example 5

23.27 g of propylene glycol monomethyl ether was added to 7.21 g of α,α,α',α'-tetrakis(4-hydroxyphenyl)-p-xylene (product name: TEP-TPA, manufactured by Asahi Organic Chemicals Industry Co., Ltd.), 7.00 g of 1-pyrenecarboxyaldehyde (manufactured by Maruzen Chemical Industries, Ltd.), and 0.29 g of methanesulfonic acid, and this mixture was stirred under reflux for 23 hours in nitrogen atmosphere. After the reaction was completed, this solution was diluted with 22 g of tetrahydrofuran. This diluted solution was subjected to reprecipitation in a mixed solvent of methanol/water (80% by mass/20% by mass). The obtained precipitate was filtered, and the residue was washed and then dried under reduced pressure at 60° C., whereby 10.2 g of a novolac resin was obtained (including the polymer of Formula (8-26)). The weight-average molecular weight measured in terms of standard polystyrene by GPC was 7,900.

Synthesis Example 6

21.02 g of propylene glycol monomethyl ether was added to 4.64 g of α,α,α',α'-tetrakis(4-hydroxyphenyl)-p-xylene (product name: TEP-TPA, manufactured by Asahi Organic Chemicals Industry Co., Ltd.), 9.00 g of 1-pyrenecarboxyaldehyde (manufactured by Maruzen Chemical Industries, Ltd.), and 0.38 g of methanesulfonic acid, and this mixture was stirred under reflux for 23 hours in nitrogen atmosphere. After the reaction was completed, this solution was diluted with 21 g of tetrahydrofuran. This diluted solution was subjected to reprecipitation in a mixed solvent of methanol/water (80% by mass/20% by mass). The obtained precipitate was filtered, and the residue was washed and then dried under reduced pressure at 60° C., whereby 10.9 g of a novolac resin was obtained (including the polymer of Formula (8-28)). The weight-average molecular weight measured in terms of standard polystyrene by GPC was 7,400.

Synthesis Example 7

22.62 g of propylene glycol monomethyl ether was added to 9.87 g of 1,1,2,2-tetrakis(3-methyl-4-hydroxyphenyl)ethane (product name: TEOC-DF, manufactured by Asahi Organic Chemicals Industry Co., Ltd.), 5.00 g of 1-pyrenecarboxyaldehyde (manufactured by Maruzen Chemical Industries, Ltd.), and 0.21 g of methanesulfonic acid, and this mixture was stirred under reflux for 23 hours in nitrogen atmosphere. After the reaction was completed, this solution was diluted with 38 g of tetrahydrofuran. This diluted solution was subjected to reprecipitation in a mixed solvent of methanol/water (50% by mass/50% by mass). The obtained precipitate was filtered, and the residue was washed and then dried under reduced pressure at 60° C., whereby 6.9 g of a novolac resin was obtained (including the polymer of Formula (8-2)). The weight-average molecular weight measured in terms of standard polystyrene by GPC was 1,700.

Synthesis Example 8

21.88 g of propylene glycol monomethyl ether was added to 4.69 g of 1,1,2,2-tetrakis(3-methyl-4-hydroxyphenyl)ethane (product name: TEOC-DF, manufactured by Asahi Organic Chemicals Industry Co., Ltd.), 9.50 g of 1-pyrenecarboxyaldehyde (manufactured by Maruzen Chemical Industries, Ltd.), and 0.40 g of methanesulfonic acid, and this mixture was stirred under reflux for 23 hours in nitrogen atmosphere. After the reaction was completed, this solution was diluted with 36 g of tetrahydrofuran. This diluted solution was subjected to reprecipitation in a mixed solvent of methanol/water (70% by mass/30% by mass). The obtained precipitate was filtered, and the residue was washed and then dried under reduced pressure at 60° C., whereby 11.5 g of a novolac resin was obtained (including the polymer of Formula (8-25)). The weight-average molecular weight measured in terms of standard polystyrene by GPC was 2,000.

Synthesis Example 9

20.65 g of propylene glycol monomethyl ether was added to 4.35 g of 1,1,2,2-tetrakis(4-hydroxyphenyl)ethane (product name: TEP-DF, manufactured by Asahi Organic Chemicals Industry Co., Ltd.), 9.00 g of 9-anthrylaldehyde, and 0.42 g of methanesulfonic acid, and this mixture was stirred under reflux for 24 hours in nitrogen atmosphere. After the reaction was completed, this solution was subjected to reprecipitation in a mixed solvent of methanol/water (60% by mass/40% by mass). The obtained precipitate was filtered, and the residue was washed and then dried under reduced pressure at 60° C., whereby 9.9 g of a novolac resin was obtained (including the polymer of Formula (8-29)). The weight-average molecular weight measured in terms of standard polystyrene by GPC was 1,300.

Synthesis Example 10

57.89 g of propylene glycol monomethyl ether was added to 9.00 g of tris(4-hydroxyphenyl)methane, 21.28 g of 1-pyrenecarboxyaldehyde (manufactured by Maruzen Chemical Industries, Ltd.), and 0.89 g of methanesulfonic acid, and this mixture was stirred under reflux for 25 hours in nitrogen atmosphere. After the reaction was completed, this solution was diluted with 63 g of tetrahydrofuran. This diluted solution was subjected to reprecipitation in methanol. The obtained precipitate was filtered, and the residue was washed and then dried under reduced pressure at 60° C., whereby 20.1 g of a novolac resin was obtained (including the polymer of Formula (8-18)). The weight-average molecular weight measured in terms of standard polystyrene by GPC was 3,200.

Synthesis Example 11

16.01 g of propylene glycol monomethyl ether was added to 5.99 g of tris(4-hydroxyphenyl)ethane, 4.50 g of 1-pyrenecarboxyaldehyde (manufactured by Maruzen Chemical Industries, Ltd.), and 0.19 g of methanesulfonic acid, and this mixture was stirred under reflux for 14 hours in nitrogen atmosphere. After the reaction was completed, this solution was diluted with 9 g of tetrahydrofuran. This diluted solution was subjected to reprecipitation in methanol/water (80% by mass/20% by mass). The obtained precipitate was filtered, and the residue was washed and then dried under reduced pressure at 60° C., whereby 4.9 g of a novolac resin was obtained (including the polymer of Formula (8-19)). The weight-average molecular weight measured in terms of standard polystyrene by GPC was 2,300.

Synthesis Example 12

5.56 g of 1,5-dihydroxynaphthalene and 8.00 g of 1-pyrenecarboxyaldehyde (manufactured by Maruzen Chemical Industries, Ltd.) were added, and this mixture was stirred under reflux for 24 hours in nitrogen atmosphere. After the reaction was completed, this solution was diluted with 35 g of tetrahydrofuran. This diluted solution was subjected to reprecipitation in methanol. The obtained precipitate was filtered, and the residue was washed and then dried under reduced pressure at 60° C., whereby 9.3 g of a novolac resin was obtained (including the polymer of Formula (12-1)). The weight-average molecular weight measured in terms of standard polystyrene by GPC was 3,100.

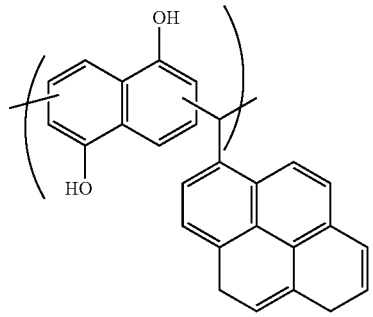

Formula (12-1)

Synthesis Example 13

22.37 g of propylene glycol monomethyl ether was added to 8.14 g of 2,2-bis[4,4-bis(4-hydroxyphenyl)cyclohexyl]propane (product name: TEP-BOCP, manufactured by Asahi Organic Chemicals Industry Co., Ltd.), 6.50 g of 1-pyrenecarboxyaldehyde (manufactured by Maruzen Chemical Industries, Ltd.), and 0.27 g of methanesulfonic acid, and this mixture was stirred under reflux for 23 hours in nitrogen atmosphere After the reaction was completed, this solution was diluted with 37 g of tetrahydrofuran. This diluted solution was subjected to reprecipitation in a mixed solvent of methanol/water (50% by mass/50% by mass). The obtained precipitate was filtered, and the residue was washed and then dried under reduced pressure at 60° C., whereby 10.4 g of a novolac resin was obtained (including the polymer of Formula (12-2)). The weight-average molecular weight measured in terms of standard polystyrene by GPC was 3,500.

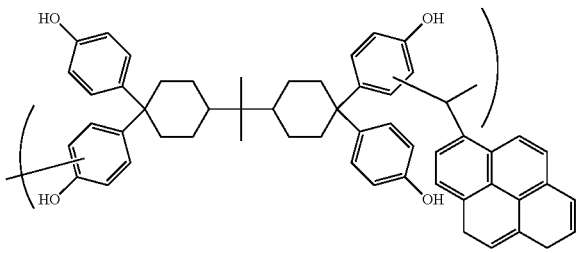

Formula (12-2)

Example 1

3.0 g of the polymer obtained in Synthesis Example 1 was dissolved in 19.2 g of propylene glycol monomethyl ether and 8.2 g of cyclohexanone, and then a solution of a resist underlayer film-forming composition used in a lithography process with a multilayer film was prepared.

Example 2

3.3 g of the polymer obtained in Synthesis Example 2 was dissolved in 20.8 g of propylene glycol monomethyl ether and 8.9 g of cyclohexanone, and then a solution of a resist underlayer film-forming composition used in a lithography process with a multilayer film was prepared.

Example 3

3.2 g of the polymer obtained in Synthesis Example 3 was dissolved in 20.1 g of propylene glycol monomethyl ether and 8.6 g of cyclohexanone, and then a solution of a resist underlayer film-forming composition used in a lithography process with a multilayer film was prepared.

Example 4

3.5 g of the polymer obtained in Synthesis Example 4 was dissolved in 22.3 g of propylene glycol monomethyl ether and 9.5 g of cyclohexanone, and then a solution of a resist underlayer film-forming composition used in a lithography process with a multilayer film was prepared.

Example 5

3.2 g of the polymer obtained in Synthesis Example 5 was dissolved in 20.2 g of propylene glycol monomethyl ether and 8.7 g of cyclohexanone, and then a solution of a resist underlayer film-forming composition used in a lithography process with a multilayer film was prepared.

Example 6

3.2 g of the polymer obtained in Synthesis Example 6 was dissolved in 20.0 g of propylene glycol monomethyl ether and 8.6 g of cyclohexanone, and then a solution of a resist underlayer film-forming composition used in a lithography process with a multilayer film was prepared.

Example 7

2.0 g of the polymer obtained in Synthesis Example 7 was dissolved in 12.6 g of propylene glycol monomethyl ether and 5.4 g of cyclohexanone, and then a solution of a resist underlayer film-forming composition used in a lithography process with a multilayer film was prepared.

Example 8

3.0 g of the polymer obtained in Synthesis Example 8 was dissolved in 18.9 g of propylene glycol monomethyl ether and 8.1 g of cyclohexanone, and then a solution of a resist underlayer film-forming composition used in a lithography process with a multilayer film was prepared.

Example 9

3.0 g of the polymer obtained in Synthesis Example 9 was dissolved in 18.9 g of propylene glycol monomethyl ether and 8.1 g of cyclohexanone, and then a solution of a resist underlayer film-forming composition used in a lithography process with a multilayer film was prepared.

Example 10

3.0 g of the polymer obtained in Synthesis Example 10 was dissolved in 18.9 g of propylene glycol monomethyl ether and 8.1 g of cyclohexanone, and then a solution of a resist underlayer film-forming composition used in a lithography process with a multilayer film was prepared.

Example 11

1.4 g of the polymer obtained in Synthesis Example 11 was dissolved in 13.0 g of propylene glycol monomethyl ether and 5.6 g of propylene glycol monomethyl ether acetate, and then a solution of a resist underlayer film-forming composition used in a lithography process with a multilayer film was prepared.

Comparative Example 1

2.0 g of the polymer obtained in Synthesis Example 12 was dissolved in 12.6 g of propylene glycol monomethyl ether and 5.4 g of cyclohexanone, and then a solution of a resist underlayer film-forming composition used in a lithography process with a multilayer film was prepared.

Comparative Example 2

2.0 g of the polymer obtained in Synthesis Example 13 was dissolved in 11.6 g of propylene glycol monomethyl ether and 5.4 g of cyclohexanone, and then a solution of a resist underlayer film-forming composition used in a lithography process with a multilayer film was prepared.

(Measurement of Pattern Bending Resistance)

Each of the solutions of the resist underlayer film-forming compositions prepared in Examples 1 to 11 and Comparative Examples 1 and 2 was applied by a spin coater onto a silicon wafer coated with a silicon oxide film. Each of them was baked on a hot plate at 400° C. for 2 minutes to form a resist underlayer film (film thickness 200 nm). Onto the resist underlayer film, a solution of a silicon hard mask-forming composition was applied, and was baked at 240° C. for 1 minute to form a silicon hard mask layer (film thickness 45 nm). Onto the silicon hard mask layer, a resist solution was applied, and was baked at 100° C. for 1 minute to form a resist layer (film thickness 120 nm). The resist layer was exposed to light having a wavelength of 193 nm with a mask, and was subjected to post exposure bake PEB (at 105° C. for 1 minute), and then development is performed to obtain a resist pattern. Thereafter, dry etching was performed with a fluorine-based gas (the component was $CF_4$) to transfer the resist pattern onto the hard mask. Then, dry etching was performed with an oxygen-based gas (the components were $O_2/CO_2$) to transfer the resist pattern onto the resist underlayer film. Subsequently, dry etching was performed with a fluorine-based gas (the components were $C_4F_6/C_4F_8/O_2/Ar$) to remove the silicon oxide film that coats the silicon wafer. Then, dry etching was performed with an oxygen-based gas (the components were $O_2/N_2$) to remove the resist underlayer film-forming composition remaining on the silicon oxide film. The shape of each pattern at each process was observed with an electron microscope. As the pattern width becomes smaller, irregular bending of the pattern called "wiggling" is more likely to occur. The above-described processes were performed with the resist underlayer film-forming compositions of these Examples, and the pattern width when such pattern bending (wiggling) started to occur was observed with an electron microscope. Because occurrence of pattern bending makes it impossible to fabricate a substrate on the basis of a faithful pattern, it is necessary to fabricate the substrate on the basis of the pattern width (critical dimension of fabrication line width) immediately before the pattern bending starts to occur. A smaller pattern width when pattern bending starts to occur enables finer fabrication of the substrate. To measure resolution, a critical dimension scanning electron microscope (manufactured by Hitachi, Ltd.) was used. The resist underlayer film-forming composition film remaining on the silicon oxide film was removed, and the fabrication line width of the silicon oxide film onto which the resist patterns were transferred in a stepwise manner was measured. The fabrication line width when the pattern formed on the silicon oxide film started to bend at this time is given in Table 1.

TABLE 1

Critical dimension of fabrication line width when pattern bending (wiggling) occurs

| Resist underlayer film-forming composition | Critical dimension of fabrication line width |
|---|---|
| Example 1 | 46.63 nm |
| Example 2 | 46.49 nm |
| Example 3 | 44.43 nm |
| Example 4 | 43.78 nm |
| Example 5 | 45.49 nm |
| Example 6 | 47.14 nm |
| Example 7 | 45.19 nm |
| Example 8 | 43.58 nm |
| Example 9 | 46.38 nm |
| Example 10 | 46.02 nm |
| Example 11 | 45.20 nm |
| Comparative Example 1 | 48.10 nm |
| Comparative Example 2 | 47.50 nm |

These results indicate that the resist underlayer film-forming compositions of Examples 1 to 10 achieved finer substrate fabrication, in which the critical dimensions of fabrication line width when the bending of the patterns formed on the silicon oxide film occurs are smaller than those of Comparative Examples 1 and 2. In other words, it was found that the resist underlayer film-forming compositions of Examples 1 to 10 exhibited useful effects for suppressing occurrence of the pattern bending (wiggling).

(Solubility Test)

Each of the solutions of the resist underlayer film-forming compositions prepared in Examples 1 to 11 and Comparative Examples 1 and 2 was dropped into propylene glycol monomethyl ether (PGME), propylene glycol monomethyl ether acetate (PGMEA), and cyclohexanone (CYH) that are common resist solvents, and whether precipitates of polymers (novolac resin components) in the resist underlayer film-forming compositions were precipitated was observed. When precipitation was not observed, the solubility of the novolac resin was rated as "excellent", and when precipitation was observed, the solubility of the novolac resin was rated as "defective". The results of the solubility tests of the novolac resin solutions are given in Table 2.

TABLE 2

Solubility test of novolac resin

| Resist underlayer film-forming composition | PGME | PGMEA | CYH |
|---|---|---|---|
| Example 1 | Excellent | Excellent | Excellent |
| Example 2 | Excellent | Excellent | Excellent |
| Example 3 | Excellent | Defective | Excellent |
| Example 4 | Excellent | Excellent | Excellent |
| Example 5 | Excellent | Excellent | Excellent |
| Example 6 | Excellent | Excellent | Excellent |
| Example 7 | Excellent | Excellent | Excellent |
| Example 8 | Excellent | Excellent | Excellent |
| Example 9 | Excellent | Excellent | Excellent |
| Example 10 | Excellent | Excellent | Excellent |
| Example 11 | Excellent | Excellent | Excellent |
| Comparative Example 1 | Defective | Defective | Excellent |
| Comparative Example 2 | Excellent | Excellent | Excellent |

From these results, it was found that the resist underlayer film-forming compositions of Examples 1 to 11 each had higher solubility in the resist solvents than that of Comparative Example 1.

(Planarizing Property Test)

Each of the solutions of the resist underlayer film-forming compositions of Examples 1 to 11 and Comparative Examples 1 and 2 was applied by a spin coater onto a wafer substrate with $SiO_2$ having lines and spaces (pattern width 75 nm, pitch width 340 nm, pattern height 80 nm) so as to achieve a film thickness of 90 nm. Each of them was baked on a hot plate at 400° C. for 2 minutes to form an underlayer film. With a scanning electron microscope (SEM), the cross-sectional shape of the wafer substrate with $SiO_2$ having the lines and spaces onto which each of the underlayer film-forming compositions for lithography obtained in Examples 1 to 11 and Comparative Examples 1 and 2 was applied was observed, and the planarizing properties of each underlayer film for the line-and-space pattern were evaluated. The result was defined as "excellent" when the underlayer film was formed on the line-and-space pattern without irregularities, the result was defined as "slightly defective" when slight irregularities were observed, and the result was defined as "defective" when irregularities were observed. The results of the planarizing property tests are given in Table 3.

TABLE 3

Planarizing property test

| Resist underlayer film-forming composition | Planarizing properties |
|---|---|
| Example 1 | Slightly Defective |
| Example 2 | Excellent |
| Example 3 | Excellent |
| Example 4 | Excellent |
| Example 5 | Excellent |
| Example 6 | Excellent |
| Example 7 | Excellent |
| Example 8 | Excellent |
| Example 9 | Excellent |
| Example 10 | Excellent |
| Example 11 | Excellent |
| Comparative Example 1 | Defective |
| Comparative Example 2 | Slightly Defective |

From these results, it was found that planarizing properties of the resist underlayer film-forming compositions of Examples 1 to 11 were better than those of Comparative Example 1.

(Embeddability Test)

Each of the solutions of the resist underlayer film-forming compositions prepared in Examples 1 to 11 and Comparative Examples 1 and 2 was applied by a spin coater onto a wafer substrate with $SiO_2$ having a hole pattern (hole diameter 120 nm, pitch width 240 nm, depth 400 nm) so as to achieve a film thickness of 200 nm. Each of them was baked on a hot plate at 400° C. for 2 minutes to form an underlayer film. With a scanning electron microscope (SEM), the cross-sectional shape of the wafer substrate with $SiO_2$ having the hole pattern onto which each of the underlayer film-forming compositions for lithography obtained in Examples 1 to 10 and Comparative Examples 1 and 2 was applied was observed, and the embeddability of the underlayer film for the hole pattern was evaluated. The result was defined as "excellent" when the underlayer film was embedded in the hole pattern without voids, and the result was defined as "defective" when the underlayer film formed voids in the hole pattern. The results of the embeddability tests are given in Table 4.

TABLE 4

Embeddability test

| Resist underlayer film-forming composition | Embeddability |
|---|---|
| Example 1 | Excellent |
| Example 2 | Excellent |
| Example 3 | Excellent |
| Example 4 | Excellent |
| Example 5 | Excellent |
| Example 6 | Excellent |
| Example 7 | Excellent |
| Example 8 | Excellent |
| Example 9 | Excellent |
| Example 10 | Excellent |
| Example 11 | Excellent |
| Comparative Example 1 | Defective |
| Comparative Example 2 | Excellent |

From these results, it was found that embeddability of the resist underlayer film-forming compositions of Examples 1 to 11 was better than that of Comparative Example 1.

INDUSTRIAL APPLICABILITY

Thus, the resist underlayer film material of the present invention used in a lithography process with a multilayer film can provide a resist underlayer film that has a selection ratio of dry etching rate close to that of a photoresist or smaller than that of the photoresist, or a selection ratio of dry etching rate smaller than that of a semiconductor substrate, unlike conventional high etch rate anti-reflective coatings, and that also has the effect of an anti-reflective coating. It was found that the film functions as a hard mask, on the basis of a comparison of the dry etching rate ratio of the film formed by baking at 400° C. with that of a phenol novolac resin in a conventional product. Accordingly, the film exhibits heat resistance to temperatures of 400° C. or above.

It was found that the underlayer film material of the present invention has such heat resistance as to enable formation of a hard mask on the top layer through evaporation.

The invention claimed is:

1. A resist underlayer film-forming composition comprising:
 a solvent; and
 a phenol novolac resin that is obtained by causing a compound that has at least three phenolic groups, in which each of the phenolic groups has a structure bonded to a tertiary carbon atom or has a structure bonded to a quaternary carbon atom to which a methyl group binds, to react with an aromatic aldehyde or an aromatic ketone in the presence of an acid catalyst.

2. The resist underlayer film-forming composition according to claim 1, wherein:
 the phenol novolac resin contains a unit structure of Formula (1), a unit structure of Formula (2), a unit structure of Formula (3), a unit structure of Formula (4), or a combination of these unit structures:

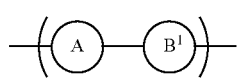

(1)

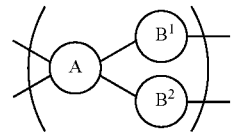

(2)

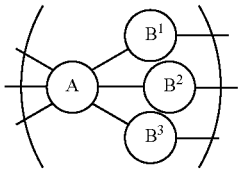

(3)

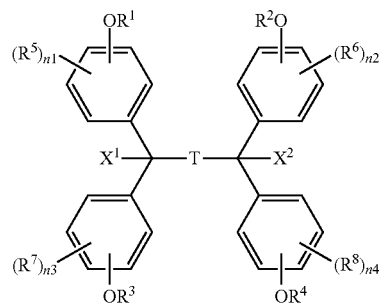

(4)

where:
 A is an organic group having at least three phenolic groups, in which each of the phenolic groups has a structure bonded to a tertiary carbon atom, and each of $B^1$, $B^2$, $B^3$, and $B^4$ is Formula (5):

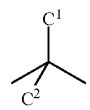

where:
 $C^1$ is a $C_{6-40}$ aryl group or a heterocyclic group that is optionally substituted with a halogen group, a nitro group, an amino group, or a hydroxy group;
 $C^2$ is a hydrogen atom or a $C_{1-10}$ alkyl group, a $C_{6-40}$ aryl group, or a heterocyclic group each of which is optionally substituted with a halogen group, a nitro group, an amino group, or a hydroxy group; and
 $C^1$ and $C^2$ optionally form a ring together with a carbon atom bonded to $C^1$ and $C^2$.

3. The resist underlayer film-forming composition according to claim 2, wherein:
 A is Formula (6):

where:
 T is a single bond, a $C_{1-10}$ alkylene group, or a $C_{6-40}$ arylene group;

$X^1$ and $X^2$ each are a hydrogen atom or a methyl group;
$R^1$ to $R^4$ each are a hydrogen atom or a $C_{1-10}$ alkyl group;
$R^5$ to $R^8$ each are a $C_{1-10}$ alkyl group or a $C_{6-40}$ aryl group;
n1 to n4 each are an integer of 0 to 3; and
each of the phenolic groups binds to $B^1$, $B^2$, $B^3$, and $B^4$.

4. The resist underlayer film-forming composition according to claim 2, wherein:
A is Formula (7):

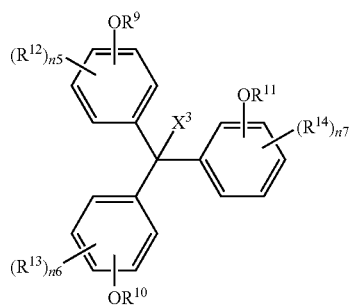

where:
$R^9$ to $R^{11}$ each are a hydrogen atom or a $C_{1-10}$ alkyl group;
$R^{12}$ to $R^{14}$ each are a $C_{1-10}$ alkyl group or a $C_{6-40}$ aryl group;
$X^3$ is a hydrogen atom or a methyl group;
n5 to n7 each are an integer of 0 to 3; and
each of the phenolic groups binds to $B^1$, $B^2$, $B^3$, and $B^4$.

5. The resist underlayer film-forming composition according to claim 2, wherein $C^1$ is an anthryl group or a pyrenyl group.

6. The resist underlayer film-forming composition according to claim 1, further comprising a cross-linking agent.

7. The resist underlayer film-forming composition according to claim 1, further comprising an acid and/or an acid generator.

8. A resist underlayer film obtained by applying the resist underlayer film-forming composition as claimed in claim 1 onto a semiconductor substrate and baking the resist underlayer film-forming composition.

9. A method for forming an underlayer film used in production of a semiconductor, the method comprising:
applying the resist underlayer film-forming composition as claimed in claim 1 onto a semiconductor substrate and baking the resist underlayer film-forming composition to form an underlayer film.

10. A method for producing a semiconductor device, the method comprising:
forming an underlayer film on a semiconductor substrate using the resist underlayer film-forming composition as claimed in claim 1;
forming a resist film on the underlayer film;
forming a resist pattern by irradiation with light or an electron beam and development;
etching the underlayer film using the resist pattern; and
processing the semiconductor substrate using the underlayer film patterned.

11. A method for producing a semiconductor device, the method comprising:
forming an underlayer film on a semiconductor substrate using the resist underlayer film-forming composition as claimed in claim 1;
forming a hard mask on the underlayer film;
further forming a resist film on the hard mask;
forming a resist pattern by irradiation with light or an electron beam and development;
etching the hard mask using the resist pattern;
etching the underlayer film using the hard mask patterned; and
processing the semiconductor substrate using the underlayer film patterned.

12. The method for producing the semiconductor device according to claim 11, wherein the hard mask is formed by evaporation of an inorganic substance.

* * * * *